US006849656B1

(12) United States Patent
Pinney et al.

(10) Patent No.: US 6,849,656 B1
(45) Date of Patent: Feb. 1, 2005

(54) INDOLE-CONTAINING AND COMBRETASTATIN-RELATED ANTI-MITOTIC AND ANTI-TUBULIN POLYMERIZATION AGENTS

(75) Inventors: Kevin Pinney, Woodway, TX (US); Feng Wang, Jeffersonville, PA (US); Mallinath Hadimani, Waco, TX (US)

(73) Assignee: Baylor University, Waco, TX (US)

( * ) Notice: Subject to any disclaimer, the term of this patent is extended or adjusted under 35 U.S.C. 154(b) by 30 days.

(21) Appl. No.: 10/070,484

(22) PCT Filed: Sep. 15, 2000

(86) PCT No.: PCT/US00/25408

§ 371 (c)(1),
(2), (4) Date: Oct. 11, 2002

(87) PCT Pub. No.: WO01/19794

PCT Pub. Date: Mar. 22, 2001

Related U.S. Application Data

(60) Provisional application No. 60/154,639, filed on Sep. 17, 1999.

(51) Int. Cl.[7] ..................... A61K 31/404; C07D 209/12
(52) U.S. Cl. ..................... 514/419; 548/491; 548/492; 548/469
(58) Field of Search .............................. 514/419, 415; 548/491, 492, 469

(56) References Cited

U.S. PATENT DOCUMENTS

| | | | |
|---|---|---|---|
| 4,133,814 A | 1/1979 | Jones et al. | 260/326.55 |
| 4,656,187 A | 4/1987 | Black et al. | 514/422 |
| 5,342,547 A | 8/1994 | Konya et al. | |
| 5,514,703 A | 5/1996 | Carlson et al. | 514/443 |
| 5,514,704 A | 5/1996 | Carlson et al. | 514/443 |
| 5,525,632 A | 6/1996 | Obsumi et al. | |
| 5,532,382 A | 7/1996 | Carlson et al. | 549/57 |
| 5,596,106 A | 1/1997 | Cullinan et al. | 549/57 |
| 5,674,906 A | 10/1997 | Hatanaka et al. | |
| 5,731,353 A | 3/1998 | Ohsumi et al. | |
| 5,886,025 A | 3/1999 | Pinney | 514/443 |
| 5,958,916 A | 9/1999 | Bryant et al. | |
| 6,110,963 A | 8/2000 | Malamas | |
| 6,162,930 A | 12/2000 | Pinney et al. | 549/57 |
| 6,166,069 A | 12/2000 | Malamas et al. | |
| 6,232,327 B1 | 5/2001 | Nickel et al. | 514/337 |
| 6,350,777 B2 | 2/2002 | Pinney et al. | 514/469 |
| 6,538,038 B1 * | 3/2003 | Pero et al. | 514/731 |
| 2002/0091148 A1 | 7/2002 | BaMaung et al. | 514/414 |

FOREIGN PATENT DOCUMENTS

| | | | | |
|---|---|---|---|---|
| EP | 1028110 A1 | 8/2000 | | 213/16 |
| WO | WO 95/10513 | 4/1995 | | |
| WO | WO 98/39323 | 9/1998 | | |
| WO | WO 00/06556 | 2/2000 | | |
| WO | 00/48606 | 8/2000 | | 31/661 |
| WO | WO 00/73264 A1 | 12/2000 | | |
| WO | 01/92224 A1 | 12/2001 | | 209/42 |
| WO | WO 02/022576 A2 | 3/2002 | | |
| WO | WO 02/36597 A1 | 5/2002 | | |
| WO | WO 02/060872 A1 | 8/2002 | | |

OTHER PUBLICATIONS

Aulakh, Chana, International Preliminary Examination Report, Mar. 27, 2002, Washington, D.C.

Banwell, et al., "Synthesis, X–Ray Crystal structure and tubulin–binding properties of a benzofuran analogue of the potent cytotoxic agent Combretastatin A–4", *Aust. J. Chem.,* 52:767–774 (1999).

Chen, et al., "Preparation of New Anti–tubulin ligands through a dual–mode, addition–elimination reaction to a bromo–substituted αβ–unsaturated sulfoxide", *J. Org. Chem.,* 65:8811–8815 (2000).

Flynn, et al., "The synthesis and tubulin binding activity of thiophene–based analogues of Combretastatin A–4", *Bioorg. Med. Chem. Lett.,* 11:2341–2345 (2001).

Flynn, et al., "A novel palladium–mediated coupling approach to 2,3–disubstituted benzo[b]thiophenes and its application to the synthesis of tubulin binding agents", *Organic Letters,* 3(5):651–654 (2001).

Gastpar, et al., "Methoxy–substituted 3–formyl–2–phenyl-indoles inhibit tubulin polymerization", *J. Med. Chem.,* 41:4965–4972 (1998).

Mahboobi, et al., "Synthetic 2–Aroylindole derivatives as a new class of potent tubulin–inhibitory, antimitotic agents", *J. Med. Chem.,* 44:4535–4553 (2001).

Pinney, et al., "A new anti–tubulin agent containing the benzo[b]thiophene ring system" *Bioorg. Med. Chem. Lett.,* 9:1081–1086 (1999).

Petit, et al., "Antineoplastic agents 389: New syntheses of the combretastatin A–4 prodrug", *Anti–Cancer Drug Design.,* 13:183–191 (1998).

* cited by examiner

*Primary Examiner*—Charanjit S. Aulakh
(74) *Attorney, Agent, or Firm*—Ivor R. Elrifi; Mintz, Levin, Cohn, Ferris, Glovsky and Popeo, P.C.

(57) ABSTRACT

Trimethoxyphenyl substituted indole ligands have been discovered which demonstrate impressive cytotoxicity as well as a remarkable ability to inhibit tubulin polymerization. Such compounds as well as related derivatives are excellent clinical candidates for the treatment of cancer in humans. In addition, certain of these ligands, as prodrugs, may well prove to be tumor selective vascular targeting and destruction chemotherapeutic agents or to have anti-angiogenesis activity resulting in the selective prevention and/or destruction of tumor cell vasculature.

39 Claims, 12 Drawing Sheets

MHEC tumor growth curve

H at position 2

INDOLE-CONTAINING AND COMBRETASTATIN-RELATED ANTI-MITOTIC AND ANTI-TUBULIN POLYMERIZATION AGENTS

This application is the U.S. national phase of PCT/US00/25408 filed Sep. 15, 2000, which claims priority to U.S. provisional application No. 60/154,639, filed Sep. 17, 1999.

BACKGROUND OF THE INVENTION

Tubulin is currently among the most attractive therapeutic targets in new drug design for the treatment of solid tumors.[1c] The heralded success of vincristine and taxol along with the promise of combretastatin A-4 (CA-4) pro-drug and dolastatin 10, to name just a few, have firmly established the clinical efficacy of these antimitotic agents for cancer treatment.

An aggressive chemotherapeutic strategy toward the treatment of solid-tumor cancers continues to rely on the development of architecturally new and biologically more potent anti-tumor, anti-mitotic agents which mediate their effect through a direct binding interaction with tubulin. A variety of clinically-promising compounds which demonstrate potent cytotoxicity and antitumor activity are known to effect their primary mode of action through an efficient inhibition of tubulin polymerization.[1] This class of compounds undergoes an initial interaction (binding) to the ubiquitous protein tubulin which in turn arrests the ability of tubulin to polymerize into microtubules which are essential components for cell maintenance and division.[2] During metaphase of the cell cycle, the nuclear membrane is broken down and the cytoskeletal protein tubulin is able to form centrosomes (also called microtubule organizing centers) and through polymerization and depolymerization of tubulin the dividing chromosomes are separated. Currently, the most recognized and clinically useful members of this class of antimitotic, antitumor agents are vinblastine and vincristine[3] along with taxol.4 Additionally, the natural products rhizoxin,[5] combretastatin A-4 and A-2,[6] curacin A,[1] podophyllotoxin,[7] epothilones A and B,[8] dolastatin 10[9] and welwistatin[10] (to name just a few) as well as certain synthetic analogues including phenstatin,[11] the 2-styrylquinazolin-4(3H)-ones (SQO),[12] and highly oxygenated derivatives of cis- and trans-stilbene[13] and dihydrostilbene are all known to mediate their cytotoxic activity through a binding interaction with tubulin. The exact nature of this binding site interaction remains largely unknown, and definitely varies between the series of compounds. Photoaffinity labeling and other binding site elucidation techniques have identified several key binding sites on tubulin: colchicine site, vinca alkaloid site, and a site on the polymerized microtubule to which taxol binds.[1a,14]

SUMMARY OF THE INVENTION

An important basic and essential aspect of this work requires a detailed understanding, on the molecular level, of the "small molecule" binding domain of both the α and β subunits of tubulin. The tertiary structure of the α, β tubulin heterodimer was reported earlier this year by Downing and co-workers at a resolution of 3.7 Å using a technique known as electron crystallography.[15] This brilliant accomplishment culminates decades of work directed toward the elucidation of this structure and should facilitate the identification of small molecule binding sites, such as the coichicine site, through techniques such as photoaffinity and chemical affinity labeling.

DETAILED DESCRIPTION OF THE INVENTION

We have developed a working hypothesis suggesting that the discovery of new antimitotic agents may result from the judicious combination of a molecular template (scaffold) which in appropriately substituted form (ie. phenolic moieties, etc.) interacts with estrogen receptor (ER), suitably modified with structural features deemed imperative for tubulin binding (arylalkoxy groups, certain halogen substitutions, etc.). The methoxy aryl functionality seems especially important for increased interaction at the colchicine binding site in certain analogs.[16] Upon formulation of this hypothesis concerning ER molecular templates, our initial design and synthesis efforts centered on benzo[b] thiophene ligands modeled after raloxifene, the selective estrogen receptor modulator (SERM) developed by Eli Lilly and Co.[17] Our initial studies resulted in the preparation of a very active benzo[b]thiophene-based antitubulin agent.[18-21] In further support of our hypothesis, recent studies have shown that certain estrogen receptor (ER) binding compounds as structurally modified estradiol congeners (2-methoxyestradiol, for example) interact with tubulin and inhibit tubulin polymerization.[22] Estradiol is, of course, perhaps the most important estrogen in humans, and it is intriguing and instructive that the addition of the methoxy aryl motif to this compound makes it interactive with tubulin. It is also noteworthy that 2-methoxyestradiol is a natural mammalian metabolite of estradiol and may play a cell growth regulatory role especially prominent during pregnancy.

Figure 1:
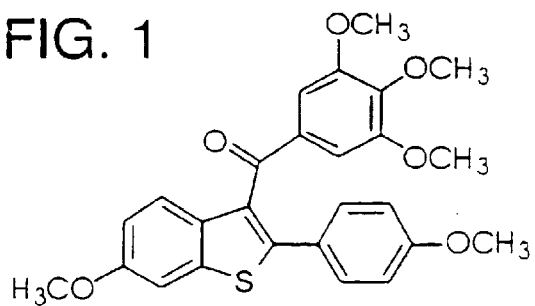
FIG. 1 illustrates 3-(3',4',5'-trimethoxybenzoyl)-2-(4'-methoxyphenyl)-6-methoxybenzo[b]thiophene.
Figure 2:
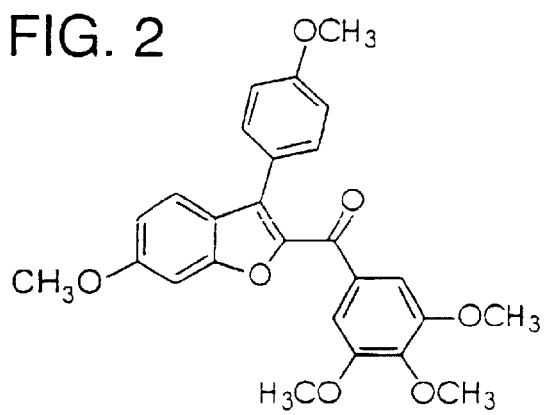
FIG. 2 illustrates 2-(3',4',5'-trimethoxybenzoyl)-3-(4'-methoxyphenyl)-6-methoxybenzo[b]furan.

The design premise that molecular skeletons of traditional estrogen receptor (ER) binding compounds can be modified with structural motifs reminiscent of colchicine and combretastatin A-4 to produce inhibitors of tubulin polymerization has been validated by the benzo[b]thiophene and benzol [b]furan classes of new antimitotic agents.[18-21] The lead compounds in each series (FIGS. 1 and 2), demonstrate remarkable biological activity against a variety of human cancer cell lines. For example, the 3,4,5-trimethoxybenzo [b]thiophene (FIG. 1) demonstrates potent cytotoxicity and inhibition of tubulin polymerization. In the NCI 60 cell line panel,[23] this compound produces a mean panel $GI_{50}=2.63\times 10^{-7}$ M (see Table I).

Inhibition of tubulin polymerization by 3-(3',4',5'-trimethoxybenzoyl)-2-(4'-methoxyphenyl)-6-methoxybenzo[b]thiophene. 50% inhibition of the maximum tubulin assembly rate with 1.1 μM drug same assay with conbretastatin A-4 gives a value of 0.73 μM.

Human cancer cell line studies (in vitro) by 3-(3',4',5'-trimethoxybenzoyl)-2-(4'-methoxyphenyl)-6-methoxybenzo[b]thiophene.

TABLE I

Inhibition of tubulin polymerization by 2-(3',4',5'-trimethoxybenzoyl)-3-(4'-methoxyphenyl)-6-methoxybenzo[b]furan. IC50 = 2.1 pM (totally flat at 4 pM).
Human cancer cell line studies (in vitro) by 2-(3',4',5'-trimethoxybenzoyl)-3-(4'-methoxyphenyl)-6-methoxybenzo[b]furan.

| Type of Cancer Cell Line | Cancer Cell Line | $GI_{50}$ (uglmL) |
|---|---|---|
| Pancreas-adn | BXPC-3 | 0.038 |
| Neuroblast | SK-N-SH | 0.025 |
| Thyroid ca | SW1736 | 0.047 |
| Lung-NSC | NCI-H460 | 0.041 |
| Pharynx-sqam | FADU | 0.035 |
| Prostate | DU-145 | 0.062 |

Figure 3:
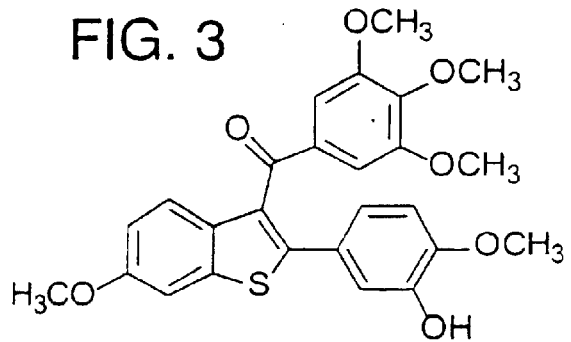
FIG. 3 illustrates benzo[b]thiophene Phenol (BBT-OH).
Figure 4:
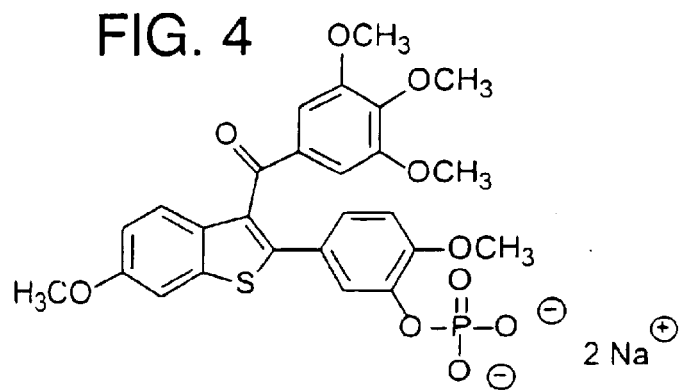
FIG. 4 illustrates benzo[b]thiophene prodrug (BBT-P).

In addition, the phenolic derivative of the 3,4-5-trimethoxybenzo[b]thiophene compound (FIG. 3) has pronounced cytotoxicity and demonstrates outstanding inhibition of tubulin polymerization[36] and the pro-drug disodium phosphate salt form of this compound (FIG. 4) demonstrates in vitro and in vivo cytotoxicity as a vascular targeting and destruction agent (which includes a component of tubulin binding (phenolic form of drug)[36, 37] and subsequent inhibition of tubulin polymerization).

Figure 5:
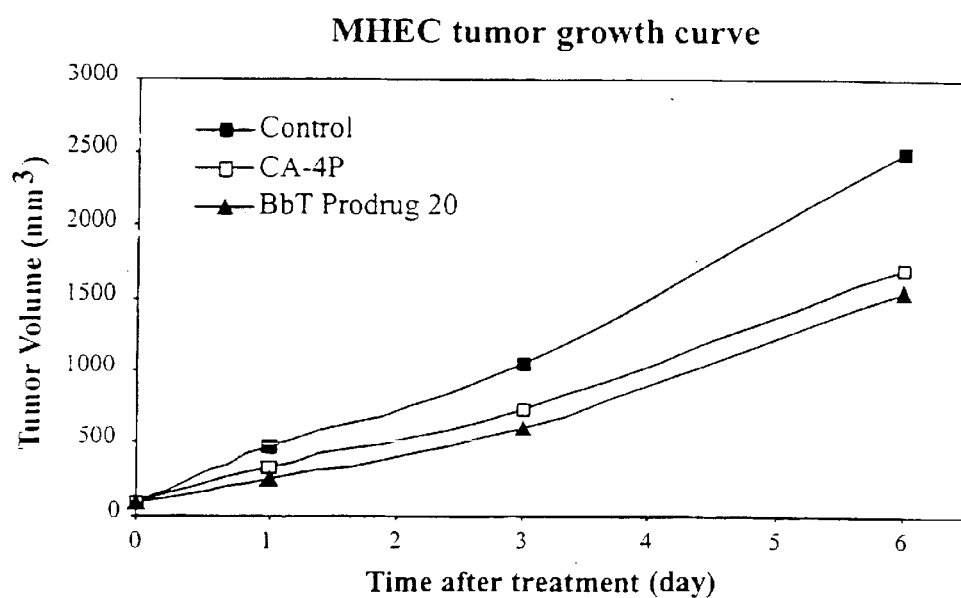
FIG. 5 illustrates in vivo biological data for benzo[b]thiophene prodrug (BBT-P).

Initial in vivo studies are very encouraging (see FIG. 5). Female scid mice were single dose ip administered with CA-4P, and benzo[b]thiophene phosphate prodrug at 400 mg/kg (i.e. MDT of CA-4P) after one week of MHEC inoculation (1×10⁻⁶/mouse). Studies were carried out through a collaboration with Professors Ronald W. Pero and Klaus Edvardsen, University of Lund, Sweden (Note: PbT Prodrug 20 is the same compound that is referred to as BBT-P).

Based on these promising research results, our interest in designing an indole based antimitotic agent was initiated, and a synthetic route (Schemes 1–4, see FIGS. 3A–D) was designed according to the synthesis of the benzo[b] thiophene derivatives.

The possibility clearly exists that some of the new indole-based ligands described herein, which are structurally related to combretastatin A-4, may also function through additional biological mechanisms involving anti-angiogenic activity. Clearly the ability to selectively disrupt the blood-flow to developing tumor cells is a potential breakthrough in the ever up-hill battle against cancer. Certain phenylindoles have been noted for inhibiting tubulin polymerization.[27]

Figure 6:
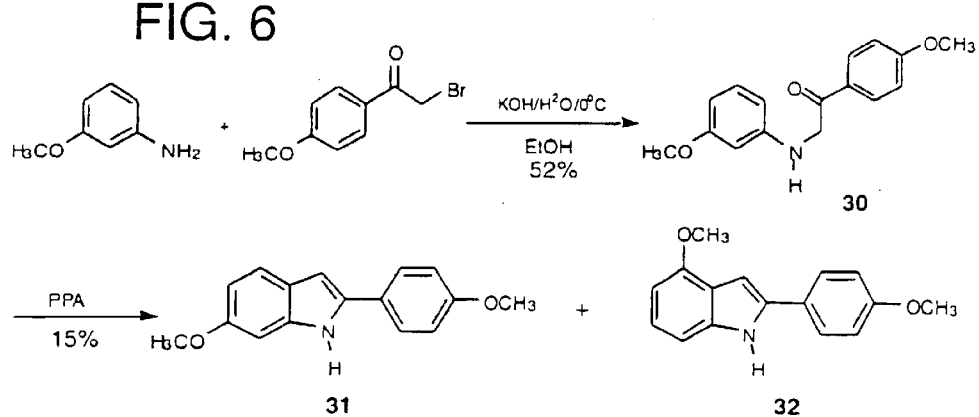
FIG. 6 illustrates a synthetic route for preparation of phenylindole derivatives.
Figure 7:
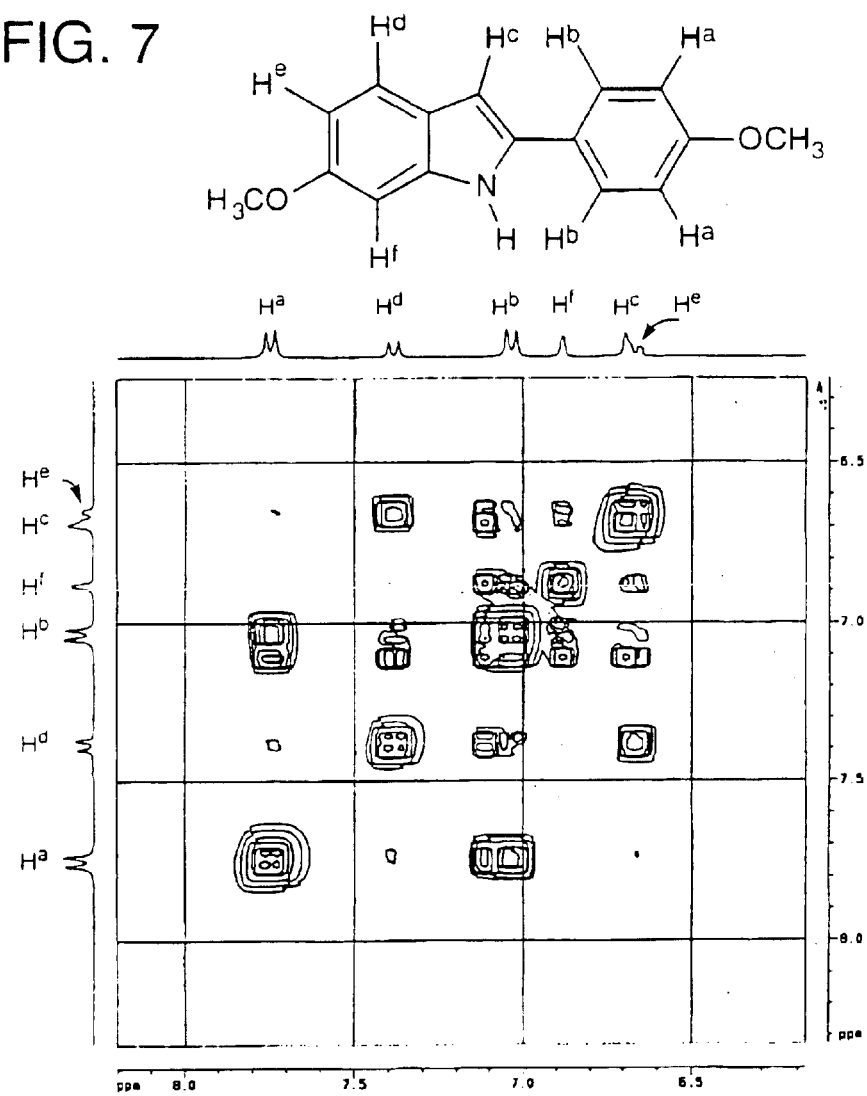
FIG. 7 illustrates a COSY NMR for 2-phenyl indole (aromatic region) a compound 31.
Figure 8:
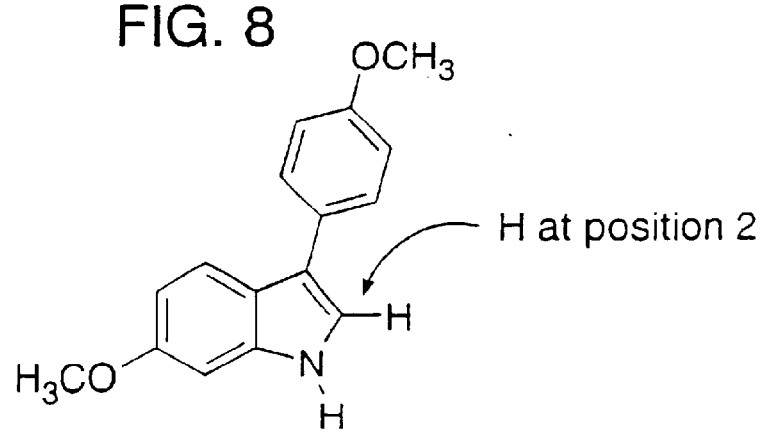
FIG. 8 illustrates a cyclized isomer without aryl migration (no evidence for its formation).
Figure 9:
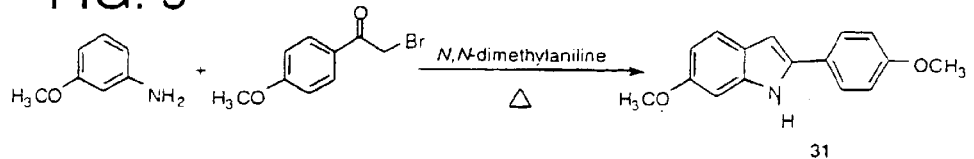
FIG. 9 illustrates a preparation of 2-phenylindole 31 in a one-pot reaction.
Figure 11:
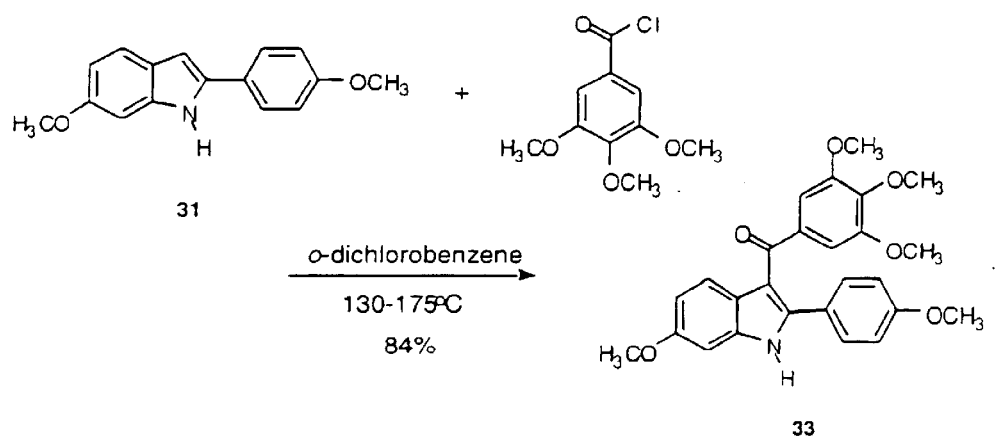
FIG. 11 illustrates a preparation of indole-based analog.

A typical synthesis of indole-based ligand 33 is shown in FIGS. 6, 9, and 11. Secondary amine 30 was prepared by treatment of m-anisidine and 2-bromo-4methoxyacetophenone under basic condition (ethanolic potassium hydroxide) at 0° C. Treatment of amine 30 with PPA resulted in the formation of two regioisomers. These isomers have poor solubility in EtOAc, $CH_2Cl_2$ and EtOH. Indole 31 was purified (from indole 32) by trituration in acetone. The structure of this isomer was confirmed by NMR analysis. COSY NMR was taken in order to study, in detail, the coupling relationship between the protons. The enlarged COSY spectrum for the aromatic region of ligand 31 is shown in FIG. 5. This COSY NMR spectrum, shows a strong coupling between $H^a$ and $H^b$ which each appear as a doublet. $H^c$ is coupled by the proton attached to the nitrogen into a small doublet. $H^d$ is coupled only by $H^e$ into a corresponding doublet, while $H^e$ is coupled both by an ortho coupling ($H^d$) and by a meta coupling ($H^f$) into a doublet of doublet pattern. $H^f$ is coupled by $H^e$ into a doublet. Further evidence of the formation of 2-phenyl indole 31 is the chemical shift of the proton $H^c$ on the ring which contains nitrogen. Though computer modeling (ChemDraw Ultra 4.5), the theoretical chemical shift value of 6.4 ppm is predicted for proton $H^c$ (at the 3 position), which matches the peak shown in the actual NMR spectrum at 6.6 ppm. For the case where the proton is at the 2 position (FIG. 8), the chemical shift is predicted to be 7.03 ppm, which does not match any peak in the spectrum that was obtained. Based collectively on these studies, the formation of isomer 31 is confirmed, and the migration of the methoxyphenyl system is evidenced. The other isomer (indole 32) is soluble in acetone and is much more difficult to obtain in pure form (see FIG. 6).

Alternatively, another synthetic methodology can also be applied to the preparation of the desired 2-phenylindole. In 1984, Angerer and co-workers reported the synthesis of 2-phenylindoles in a one-pot reaction sequence FIG. 9) as a route toward the development of new therapeutic agents for the treatment of endocrine disorders.[25]

Following this procedure (FIG. 9), two arylindole regioisomers were obtained in good yield. Recrystallization in EtOH afforded the desired isomer, 2-phenylindole 31, as a white crystalline material.

Figure 10:
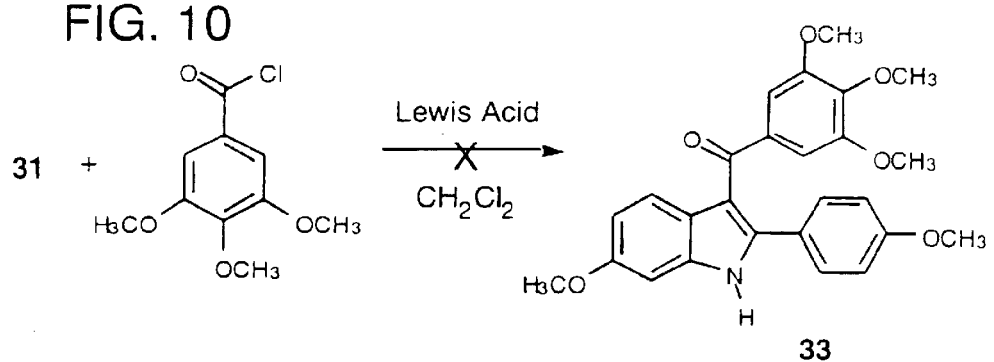
FIG. 10 illustrates a designed synthetic route for preparation of indole-based analog.

In order to synthesize the indole-based analog 33, Friedel-Crafts acylation was carried out by treating indole 31 with 3,4,5-trimethoxybenzoyl chloride in the presence of the Lewis-Acid $AlCl_3$ (FIG. 10). The reaction did not work under the regular conditions and only starting material was obtained following work-up. Attempts to modify the reaction conditions by increasing the reaction temperature or using other Lewis Acids, such as $TiCl_4$, proved futile as well. Starting material was recovered in all cases. One possible explanation for this result is the fact that the nitrogen atom (containing a lone pair of electrons and an acidic proton) may disrupt the acylation process. According to this analysis, a Grignard reagent (ethylmagnesium bromide) was used to protect this nitrogen prior to the Friedel-Crafis acylation step. Still, only starting material was obtained following the reaction. Therefore, a new synthetic approach was brought into this study.

In 1977, Inion and co-workers reported the synthesis of a variety of aminoalkoxy4-benzoyl-3-indoles.[26] The benzoate indole product was prepared by treatment of indole with the appropriate benzoyl chloride with heating (130–150° C). HCl is generated under these conditions. A similar synthetic approach was used in the synthesis of the desired trimethoxybenzoate indole ligand 33 (FIG. 11).

The precursor, indole 31, was mixed with trimethoxybenzoyl chloride. Since both reagents are solid, a solvent with a high boiling point was needed. 1,2-dichlorobenzene was chosen in this case since it has a boiling point of 180° C. Under these condition, indole 33 was obtained in moderate yield following purification by flash column chromatography and recrystallization. NMR spectroscopy suggests that the structure of indole 33 is that indicated in FIG. 11.

Figure 12:
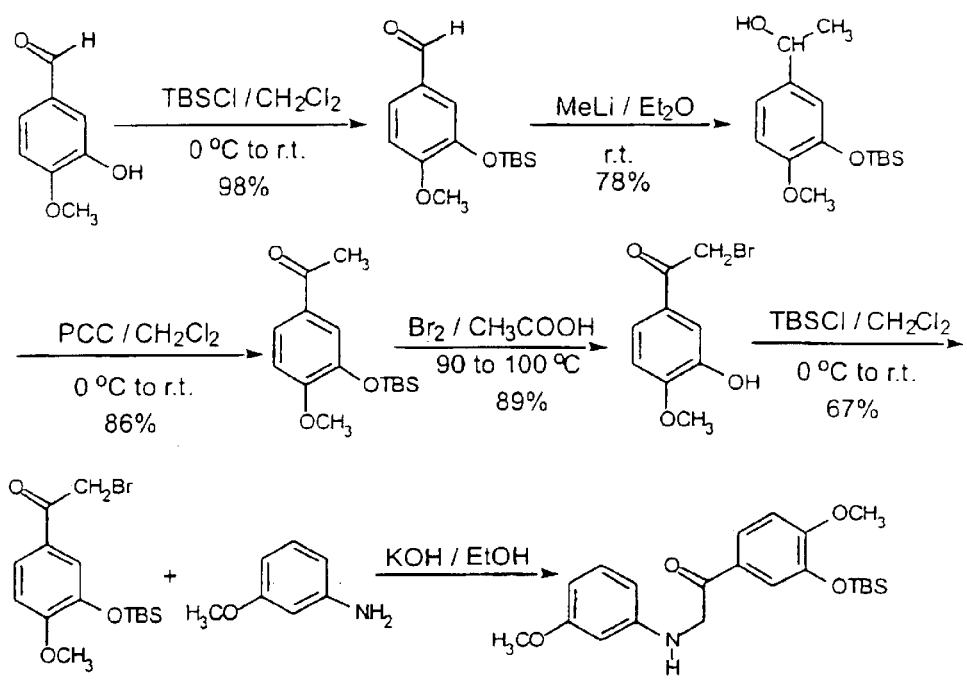
FIG. 12 illustrates a synthesis of indole-based disodium prodrug salt.
Figure 13:
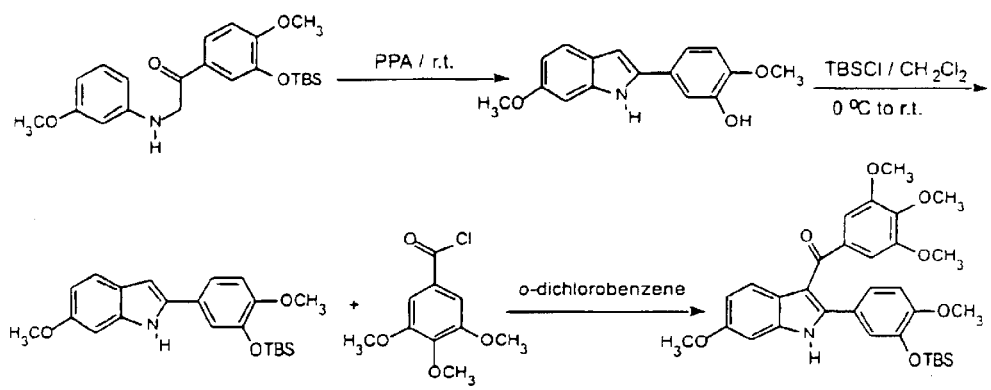
FIG. 13 illustrates another synthesis of indole-based disodium prodrug.
Figure 14:
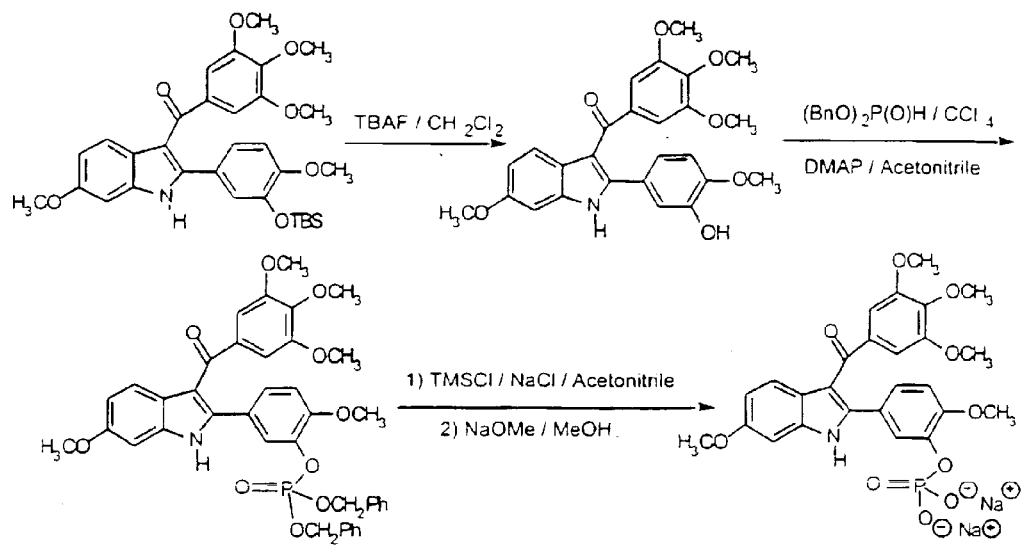
FIG. 14 illustrates another synthesis of indole-based disodium prodrug.
Figure 15:
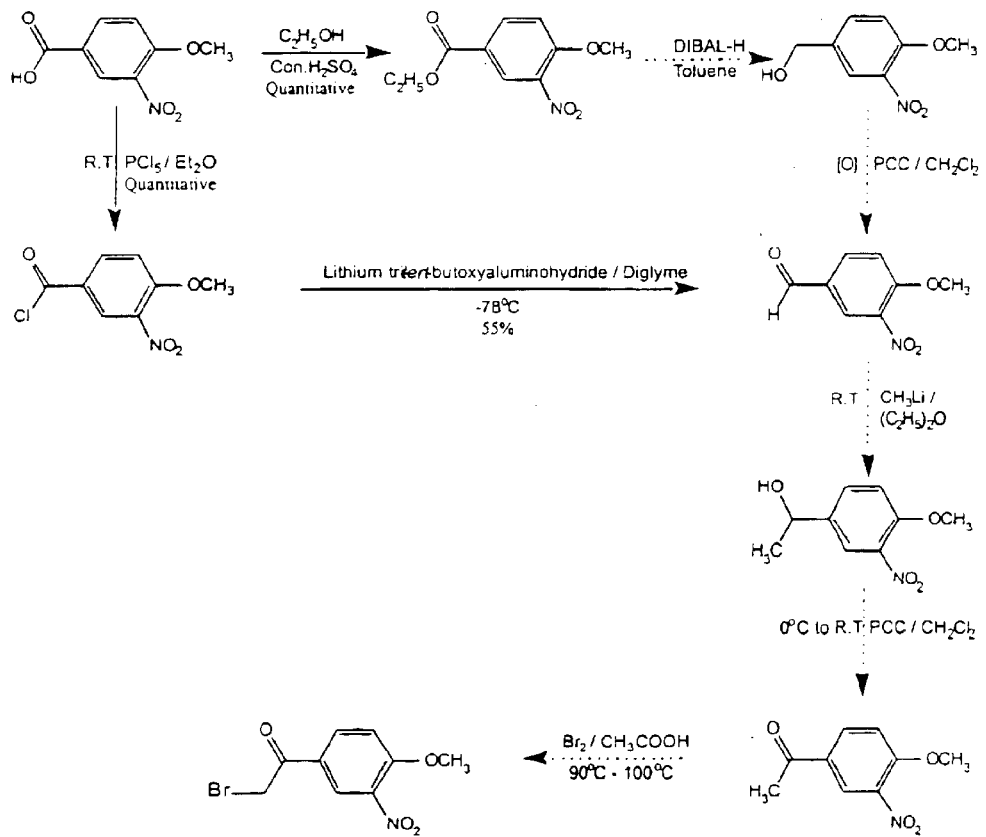
FIG. 15 illustrates a synthesis of indole based phosphoramidate prodrug.
Figure 16:
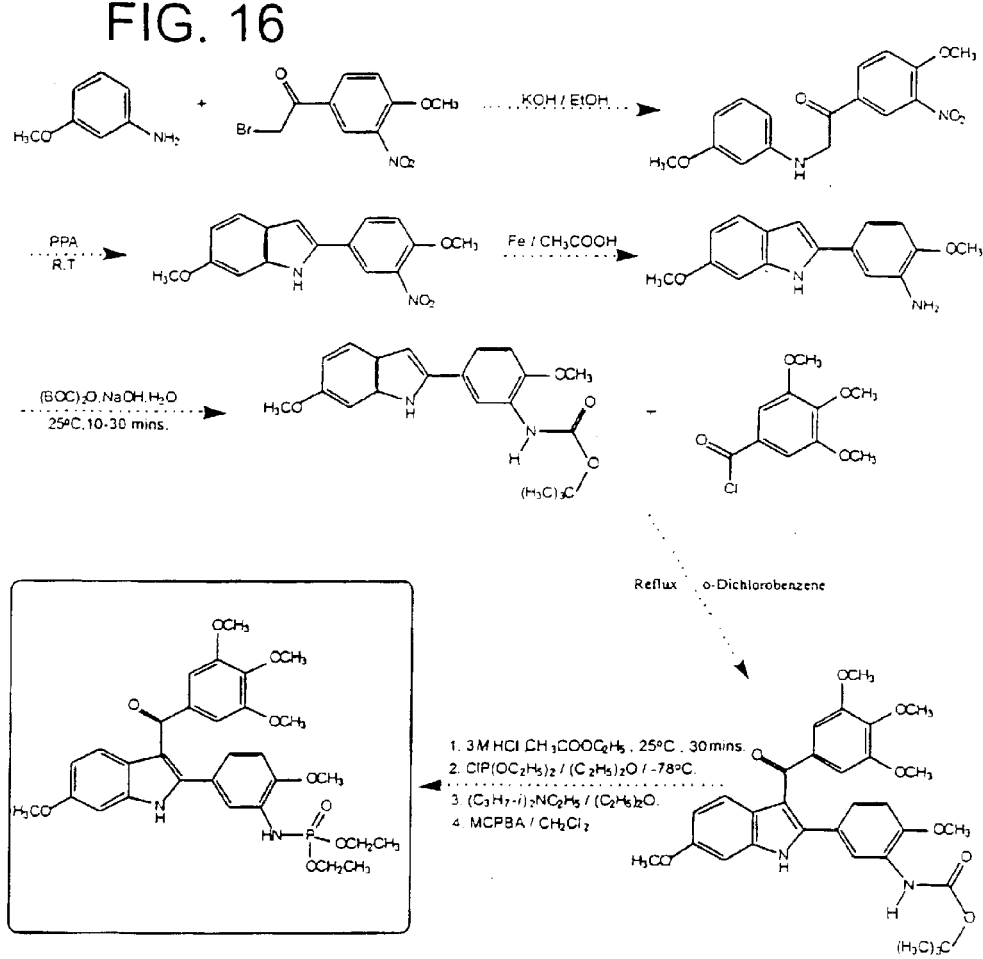
FIG. 16 illustrates another synthesis of indole-based disodium prodrug salt.

Based on promising results obtained with benzo[b] thiophene and benzofuran analogs, the preparation of phosphate salts is detailed in FIGS. 12–14, the preparation of analogs is detailed in FIGS. 15–16 and the preparation of similar indole-based phosphate prodrug salts and phosphoramidate derivatives is detailed in FIGS. 21–51.

In addition to the phosphate ester prodrugs that are described in this application for indole-based anti-mitotic agents, we have also discovered that phosphorous based prodrug derivatives of the nitrogen analog of combretastatin A-4 (CA-4) may have therapeutic advantages as selective tumor vasculature destruction agents. These compounds are primarily phosphoramidate derivatives and related phosphate dianions that are assembled on the 3Æ amino substituent of the nitrogen analog of CA-4. Although we describe two specific compounds and several obvious analogs, it should be apparent to anyone skilled in the art, that there are numerous other nitrogen phosphorous bond designs that might be assembled from the 3-amino-combretastatin A-4 structure and that would display similar functionality as prodrugs for the selective destruction of tumor vasculature.

Figure 17A:
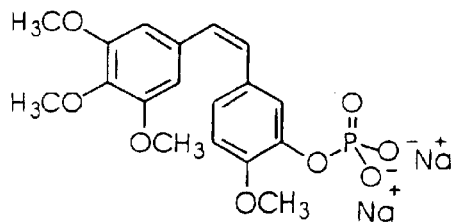
FIG. 17A illustrates a combretastatin A-4 pro-drug.

Further significance is given to new drugs that bind to the coichicine site since it has recently been shown that combretastatin CA-4 also demonstrates anti-angiogenesis activity.[24] An emerging area of cancer chemotherapy centers on the development of both anti-angiogenesis drugs which disrupt the new microvessel formation of developing tumors and vascular targeting and destruction agents which selectively target the vasculature of tumor cells while leaving healthy cells intact. Combretastatin CA-4P prodrug (FIG. 17A) is one of the leading new candidates from among a relatively small collection of known world compounds which display this vaxcular targeting. Discovered by Professor George R. Pettit (Arizona State University) from a willow tree (*combretum caffrum*) in South Africa in the 1970s, this compound is currently undergoing phase I clinical evaluation sponsored and licensed by OXiGENE, Inc.

Combretastatin A-4 (CA-4) is a potent inhibitor of tubulin polymerization which binds to the colchicine site on β-tubulin. Interestingly, CA-4 itself does not demonstrate destruction of tumor vasculature, while CA-4 prodrug is very active in terms of tumor vasculature destruction. It is very likely that the phosphate ester portion of the prodrug undergoes dephosphorylation (perhaps through the action of endothelial alkaline phosphatases) selectively at sites of enhanced vascularization to reveal the potent CA-4 itself which destroys the tumor cell through an inhibition of tubulin polymerization. The dephosphorylation event takes place selectively at tumor cells since tumor cells represent sites of prolific vascularizaton and alkaline phosphatases appear to be present at elevated concentrations in the endothelial cells lining tumor vasculature. This need for enhanced vascularization is not necessary for healthy cells. Hence, this dual-mode reactivity profile is clearly important in order to target tumor cells selectively over healthy cells. This is a proposal which has been advanced by Professor Ronald Pero (OXiGENE, Inc., University of Lund) for which a variety of strong evidence has been obtained.

Figure 17B:
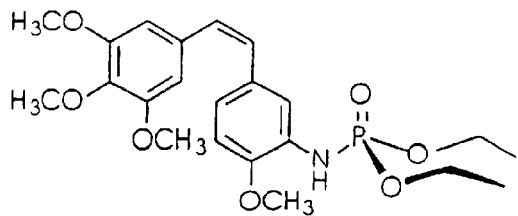
FIG. 17B illustrates a phosphoramidate analog 10.

Based in part on the good and promising biological results obtained for the 3'-nitrogen analogs of combretastatin A-4, a phosphoramidate analog has been prepared as a new combretastatin A-4 nitrogen prodrug (FIG. 17B).

Figure 18:
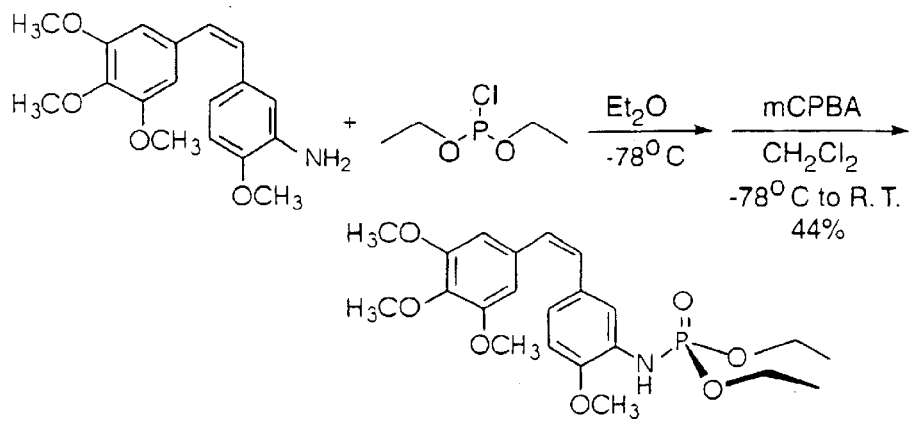
FIG. 18 illustrates a synthesis of phosphoramidate 10.

Phosphoramidate 10 below was obtained following the procedure reported by Taylor and coworkers for unrelated aryl amines.[28] Treatment of arylamine 7B with diethylchiorophosphite in anhydrous ether followed by oxidation with m-CPBA produced the phosphoramidate 10 in moderate yield (FIG. 18).

Figure 19:
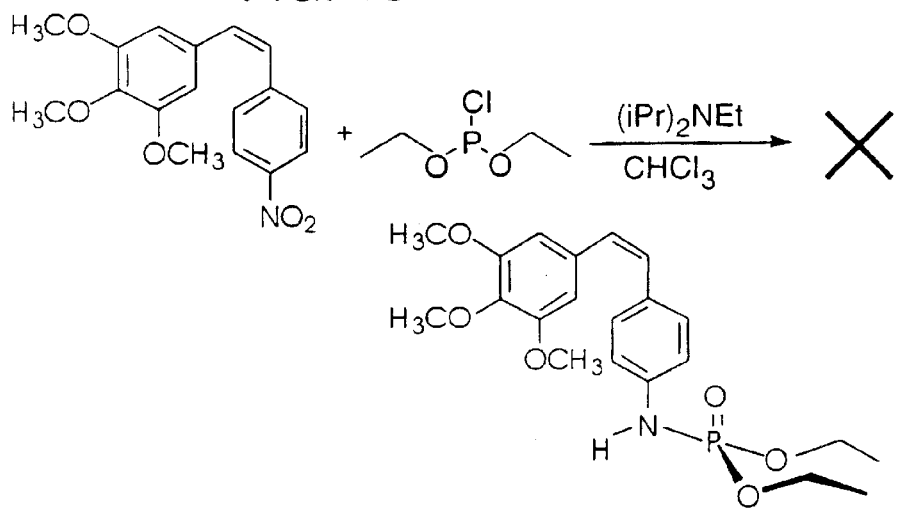
FIG. 19 illustrates a model system used for phosphoramidate synthesis.
Figure 20:
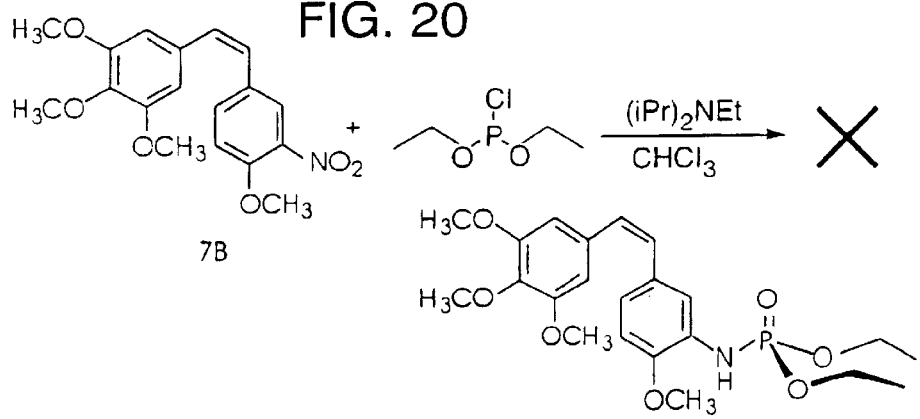
FIG. 20 illustrates a synthesis of phosphoramidate 10 from from (Z)-3'-nitro combrestastatin analog 7B.
Figure 21:
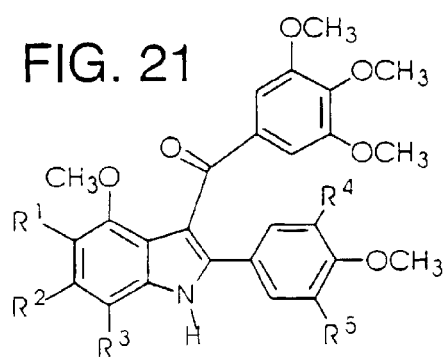
FIG. 21 illustrates substituted 4-methoxyindole amines and/or phenols.
Figure 22:
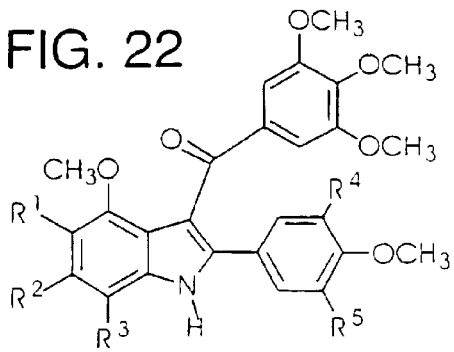
FIG. 22 illustrates substituted 4-methoxyindole phosphate ester moieties and phosphoramidates.
Figure 23:
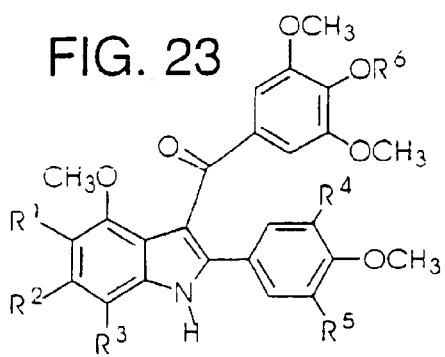
FIG. 23 illustrates further substituted 4-methoxyindole phosphate ester moieties and phosphoramidates.
Figure 24:
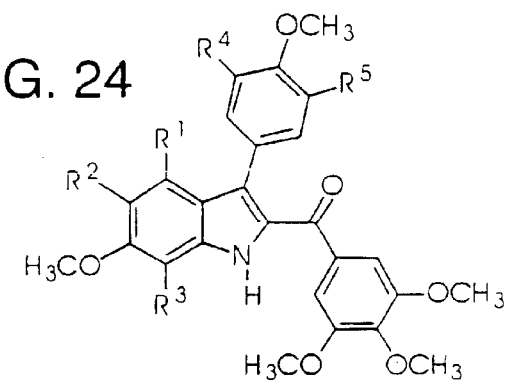
FIG. 24 illustrates substituted 6-methoxyindole amines and/or phenols.
Figure 25:
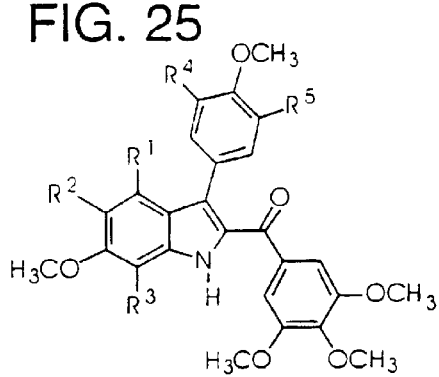
FIG. 25 illustrates substituted 6-methoxyindole phosphate ester moieties and phosphoramidates.
Figure 26:
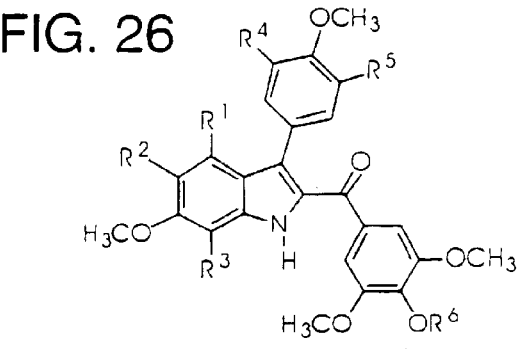
FIG. 26 illustrates substituted 6-methoxyindole phosphate ester moieties and phosphoramidates.
Figure 27:
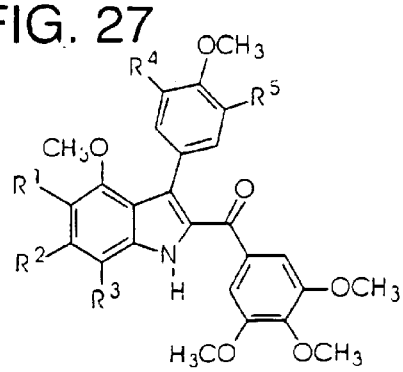
FIG. 27 illustrates substituted 4-methoxy-3-arylindole amines and/or phenols.
Figure 28:
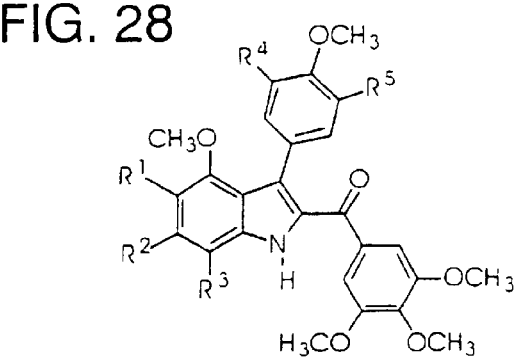
FIG. 28 illustrates substituted 4-methoxy-3-arylindole phospate moieties and phosphoramidates.
Figure 29:
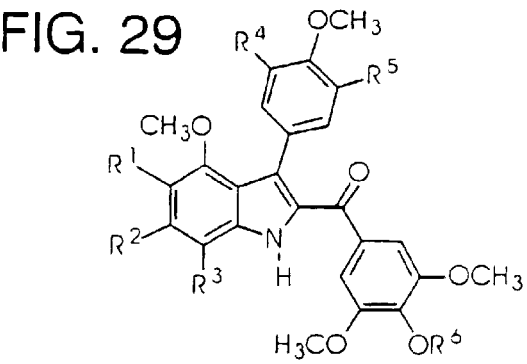
FIG. 29 illustrates further substituted 4-methoxy-3-arylindole phospate moieties and phosphoramidates.
Figure 30:
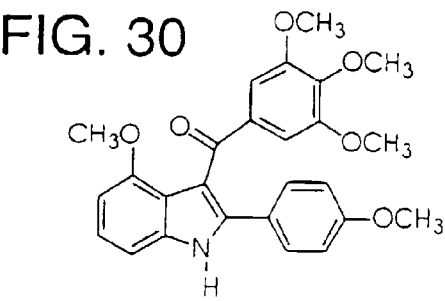
FIG. 30 illustrates 2-(4'-Methoxyphenyl)-3-(3",4",5"-trimethoxybenzoyl)-4-methoxyindole.
Figure 31:
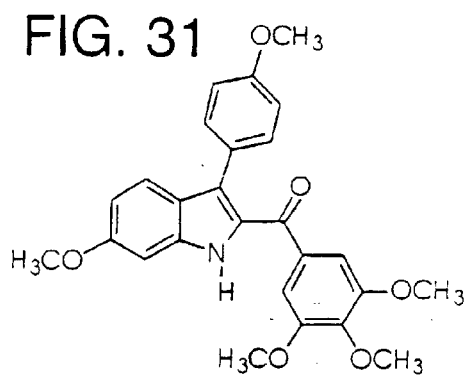
FIG. 31 illustrates 2-(3',4',5'-Trimethoxybenzoyl)-3-(4"-methoxyphenyl)-6-methoxyindole.
Figure 32:
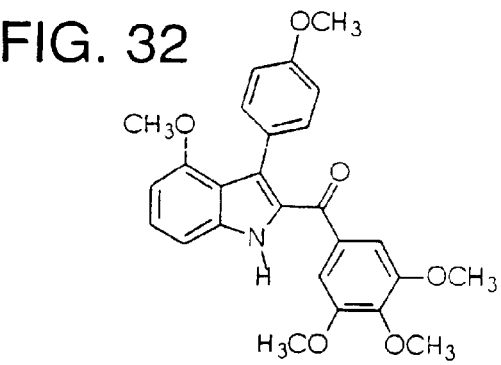
FIG. 32 illustrates 2-(3',4',5'-Trimethoxybenzoyl)-3-(4"-methoxyphenyl)-4-methoxyindole.
Figure 33:
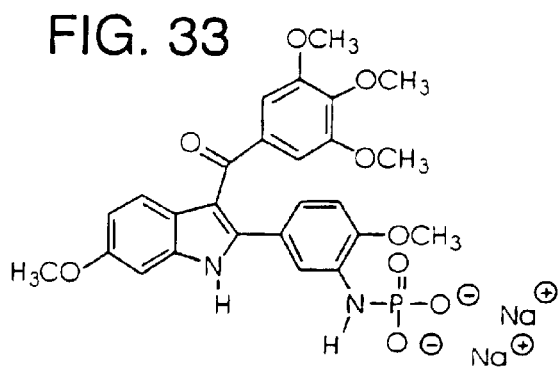
FIG. 33 illustrates Disodium 2-(3'-phosphoramidate-4'-methoxyphenyl)-3-(3",4",5"-trimethoxybenzoyl)-6-methoxyindole.
Figure 34:
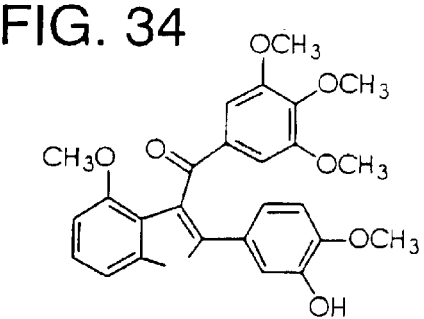
FIG. 34 illustrates 2-(3'-Hydroxy-4'-methoxyphenyl)-3-(3",4",5"-trimethoxybenzoyl)-4-methoxyindole.
Figure 35:
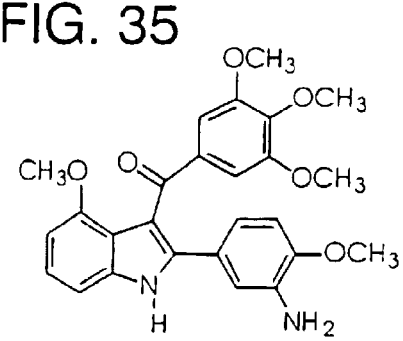
FIG. 35 illustrates 2-(3'-Amino-4'-methoxyphenyl)-3-(3",4",5"-trimethoxybenzoyl)-4-methoxyindole.
Figure 36:
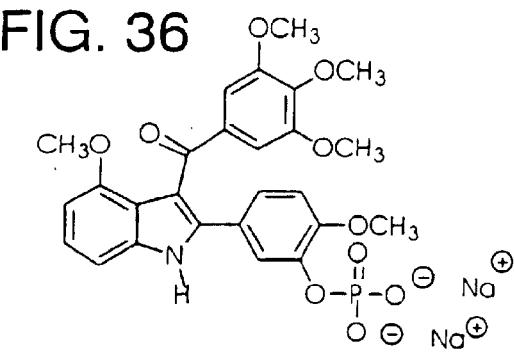
FIG. 36 illustrates Disodium 2-[(4'-methoxyphenyl)-3'-O-phosphate]-3-(3",4", 5"trimethoxybenzoyl)-4-methoxyindole.
Figure 37:
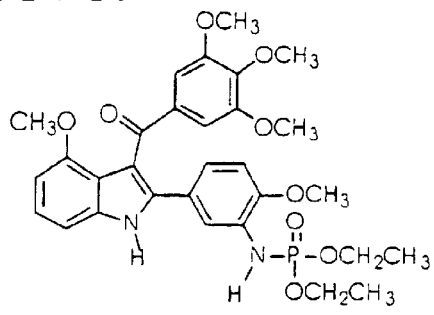
FIG. 37 illustrates 2-(3'-Diethylphosphoramidate-4'-methoxyphenyl)-3-(3",4",5"-trimethoxybenzoyl)-4-methoxyindole.
Figure 38:
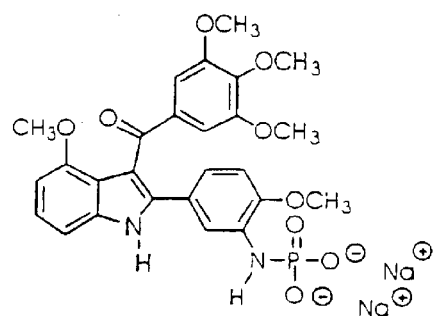
FIG. 38 illustrates Disodium 2-(3'-phosphoramidate-4'-methoxyphenyl)-3-(3",4",5"-trimethoxybenzoyl)-4-methoxyindole.
Figure 39:
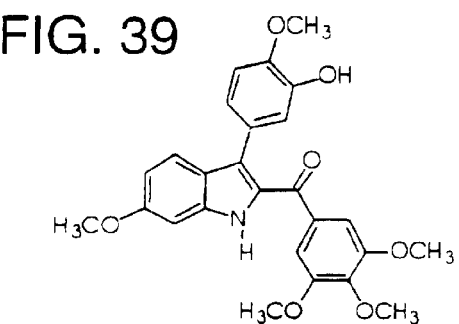
FIG. 39 illustrates 2-(3',4',5'-trimethoxybenzoyl)-3-(3"-hydroxy-4"-methoxyphenyl)-6-methoxyindole.
Figure 40:
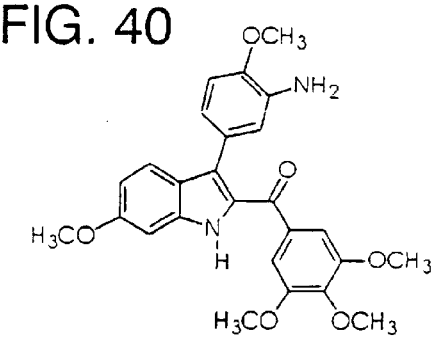
FIG. 40 illustrates 2-(3',4',5'-trimethoxybenzoyl)-3-(3"-amino-4"-methoxyphenyl)-6-methoxyindole.
Figure 41:
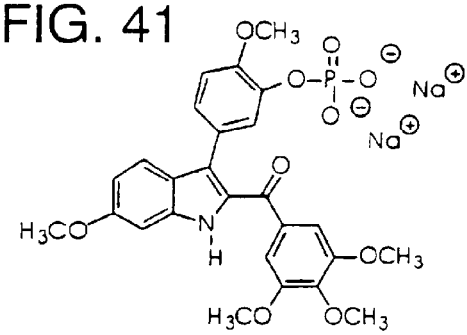
FIG. 41 illustrates Disodium 2-(3',4',5'-trimethoxybenzoyl)-3-[(4"-methoxyphenyl-3"-O-phosphate)]-6-methoxyindole.
Figure 42:
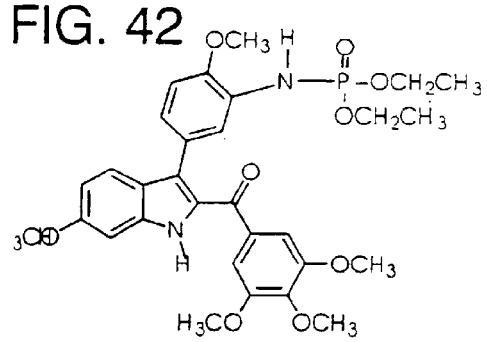
FIG. 42 illustrates 2-(3',4',5'-trimethoxybenzoyl)-3-[(4"-methoxyphenyl-3"-diethylphosphoramidate)]-6-methoxyindole.
Figure 43:
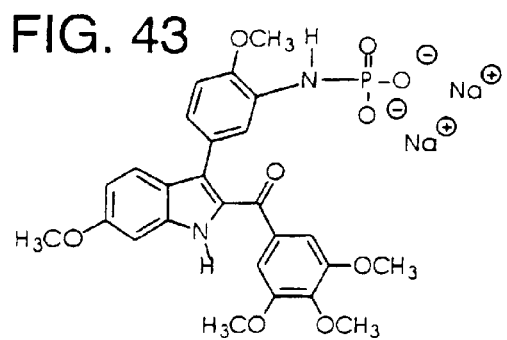
FIG. 43 illustrates Disodium 2-(3',4',5'-trimethoxybenzoyl)-3-[(4"-methoxyphenyl-3"-phosphoramidate)]-6-methoxyindole.
Figure 44:
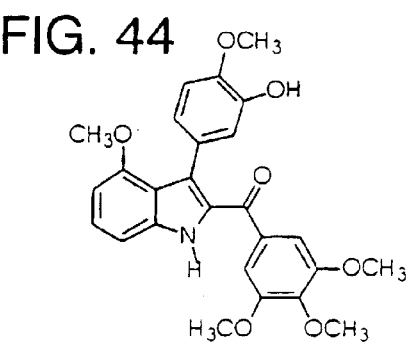
FIG. 44 illustrates 2-(3',4',5'-trimethoxybenzoyl)-3-(3"-hydroxy-4"-methoxyphenyl)-4-methoxyindole.
Figure 45:
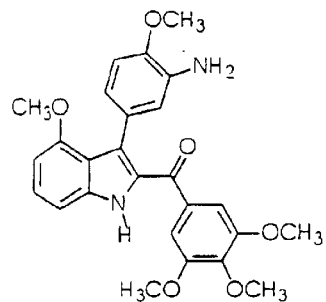
FIG. 45 illustrates 2-(3',4',5'-trimethoxybenzoyl)-3-(3"-amino-4"-methoxyphenyl)-4-methoxyindole.
Figure 46:
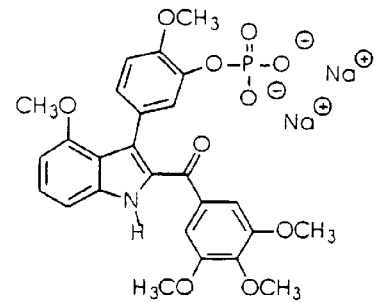
FIG. 46 illustrates Disodium 2-(3',4',5'-trimethoxybenzoyl)-3-[(4"-methoxyphenyl-3"-O-phosphate)]-4-methoxyindole.
Figure 47:
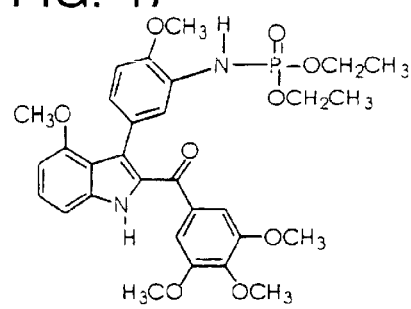
FIG. 47 illustrates 2-(3',4',5'-trimethoxybenzoyl)-3-[(4"-methoxyphenyl-3"-diethylphosphoramidate)]-4-methoxyindole.
Figure 48:
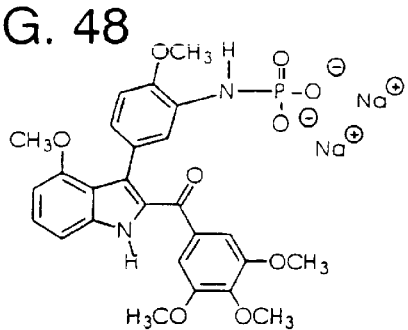
FIG. 48 illustrates Disodium 2-(3',4',5'-trimethoxybenzoyl)-3-[(4"-methoxyphenyl-3"-phosphoramidate)]-4-methoxyindole.
Figure 49:
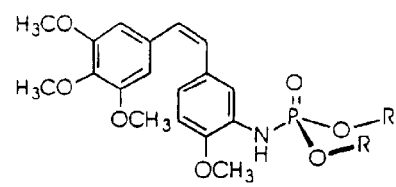
FIG. 49 illustrates substituted 3-phosphoramidate derivatives of combretastatin A-4.
Figure 50:
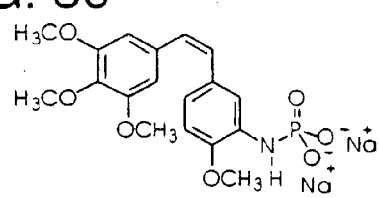
FIG. 50 illustrates Disodium (Z)-1-[(4'-methoxyphenyl)-3'-phosphoramidate]-2-(3",4",5"-trimethoxyphenyl)ethene
Figure 51:
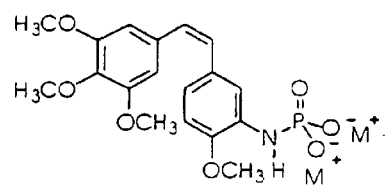
FIG. 51 illustrates substituted 3-phosphoramidate salts of combretastatin A-4.

A previous attempt in the synthesis of the phosphoramidate analog 10 utilized the methodology reported by Bilha Fisher and Larisa Sheihet.[29] This methodology presents a phosphoramidate intermediate, which can be isolated from the reduction of nitro aryl compounds to the corresponding aryl amines using diethylchlorophosphite as a biphilic reagent. The (Z)-nitro combretastatin analog 7B was considered a viable starting material for the synthesis of the phosphoramidate prodrug 10. This reaction was also tried using (Z)-1-(3',4',5'-trimethoxyphenyl)-2-(4''-nitrophenyl) ethene (synthesized in a similar manner as the other combretastatin containing analogs reported previously) as a model system (FIG. 19). In neither case was the phosphoramidate product observed. It is thought that the presence of methoxy groups as strong electron donating substituents on the stilbene system disfavors the reaction (FIG. 20).

It should be obvious to anyone skilled in the art of phosphate of phosporamidate chemistry that there are numerous other synthetic methods which can be employed to prepare phosphoramidates (such as 10) and their related salts (—NHPO$_3^{-2}$2Na$^+$).

TABLE II

[30]In vitro Human Cancer Cell Line Study of Phosphoramidate Analog 10. GI$_{50}$, TGI, and LC$_{50}$ are reported as concentrations in μg/mL ND = Not determined

| Cell Type | Cell Line | GI$_{50}$ | TGI | LC$_{50}$ |
|---|---|---|---|---|
| Pancreas-a | BXPC-3 | 1.5 × 10$^{-1}$ | 5.7 × 10$^{-1}$ | >10 |
| Ovarian | OVCAR-3 | 1.9 × 10$^{-1}$ | 8.6 × 10$^{-1}$ | >10 |
| CNS | SF-295 | 2.4 × 10$^{-1}$ | >10 | >10 |
| Lung-NSC | NCI-H460 | 3.5 × 10$^{-1}$ | >10 | >10 |
| Colon | KM20L2 | 2.8 × 10$^{-1}$ | 6.1 × 10$^{-1}$ | >10 |
| Prostate | -DU-145 | 2.6 × 10$^{-1}$ | 2.6 × 10$^{-1}$ | >10 |
| Leukemia | P388 | 3.1 × 10$^{-1}$ | ND | ND |

Biological evaluation (in vitro) suggests that the phosphoramidate prodrug 10 is less effective than the corresponding amine 8 (Table II). Pettit and co-workers reported a similar loss in biological activity in vitro for the phosphate prodrugs of combretastatin A-4 and phenstatin compared to the original compounds (Table III).[31] These results might be explained by the bulkiness of the phosphorous group and its steric hindrance toward binding site recognition. In fact, Pettit and co-workers reported no inhibition of tubulin polymerization with the combretastatin prodrug while only a 40% activity is present for the phenstatin prodrug compared to phenstatin. The IC$_{50}$ values for inhibition of tubulin polymerization are 1.2±0.1 μM for CA-4, >80 μM for CA-4 prodrug, 1.0±0.2 μM for phenstatin and 21±3 μM for phenstatin prodrug; similar results are expected for the amino-CA-4 8 and the phosphoramidate 10.[31] The IC$_{50}$ for the amino-CA-4 8 is 1.2±0.02 μM, and the phosphoramidate 10 has little if any activity.[32]

TABLE III

Comparative GI$_{50}$ Values Against Human Cancer Cell Lines for Amine-CA-4 8, Amine-CA-4 Prodrug 10, Phenstatin, Phenstatin Prodrug and Combretastatin A-4 Prodrug. GI$_{50}$, values are reported as concentrations in μg/mL ND = Not determined,
[a]Data obtained in collaboration with Dr. George R. Pettit.
[30b]Data obtained from synthesis of phenstatin phosphate.

| Cell Type | Cell-Line | Amine-CA-4 8[a] | Amine-CA-4 Prodrug 10[a] | Phenstatin | Phenstatin Prodrug[b] | Combretastatin A-4 Prodrug[b] |
|---|---|---|---|---|---|---|
| Ovarian | OVCAR-3 | ND | 1.9 × 10$^{-1}$ | 2.3 × 10$^{-3}$ | 2.5 × 10$^{-3}$ | 2.3 × 10$^{-2}$ |
| CNS | SF-295 | ND | 2.4 × 10$^{-1}$ | 5.2 × 10$^{-2}$ | 1.2 × 10$^{-2}$ | 3.6 × 10$^{-2}$ |
| Lung-NSC | NCI-H460 | 6.8 × 10$^{-4}$ | 3.5 × 10$^{-1}$ | 5.7 × 10$^{-3}$ | 3.5 × 10$^{-2}$ | 2.9 × 10$^{-2}$ |
| Colon | KM20L2 | ND | 2.8 × 10$^{-1}$ | 4.0 × 10$^{-4}$ | 2.7 × 10$^{-1}$ | 3.4 × 10$^{-1}$ |

In terms of in vivo systems, phosphoramidate analog 10 is able to provide a more soluble compound than the amine 8, thereby incrementing its bioavailability. Under, in vivo biological conditions, the P-N bond can be broken by serum phosphatases releasing the amine which can inhibit tubulin polymerization in a manner analogous to combretastatin Anti-Angiogenesis The growth of a tumor depends on the generation of blood vessels which will provide all the metabolites required during cell division. The development of anti-angiogenic compounds is especially useful in the treatment of solid tumors, since these compounds have the potential capability of selectively disrupting the vasculature of tumor cells while leaving healthy cells in a viable situation. The combretastatin A-4 prodrug has demonstrated anti-angiogenic activity since small doses of the drug are toxic to tumor vasculature.[34] Enhanced cytotoxic activity was observed against endothelial cells associated with the tumor vasculature of cancerous cells, while at the same time it was reported to have no effect against other endothelial cells which are located distant from the tumor itself.[34, 35] The mechanism of action of combretastatin A-4 prodrug, as an anti-angiogenic drug for cancer treatment, is under investigation because the development of blood vessels is crucial for the survival and growth of solid tumors. One proposed mechanism for anti-angiogenesis involves induction of apoptosis (cell suicide) of the cells instead of necrosis. An evaluation of the ability of the new phosphoramidate 10, along with structurally similar compounds, to induce apoptosis of endothelial cells will be undertaken in the near future.

Synthesis of the Phosphoramidate Analog

(Z)-1-(3'-Diethylphosphoramidate-4'-methoxyphenyl)-2-(3",4",5"-trimethoxyphenyl) ethene 10

Diethylchlorophosphite (0.103 g, 0.66 mmol) was dissolved in anhydrous diethyl ether (2.5 ml) and cooled to −78° C. Diisopropylethyl amine (0.187 g. 1.45 mmol) was dissolved in $Et_2O$ (1.0 ml) and added slowly over a period of 2 mm to the reaction mixture by syringe. Amino-stilbene 8 was dissolved in $Et_2O$ (1.0 mL) and added slowly to the reaction mixture by syringe. The reaction mixture was stirred under nitrogen at −78° C. for 2 hours, followed by stirring for 1 hour at room temperature. The mixture was filtered, and the solvent was removed under reduced pressure. A yellow oil was obtained which was dissolved in dry $CH_2Cl_2$ (5 mL). The oil was cooled to −40° C. and a solution of m-CPBA (0.193 g, 1.12 mmol) in $CH_2Cl_2$ (5 mL) was added. It was stirred over one hour at room temperature. After this time, the reaction mixture was cooled to −40° C. and filtered through a sintered glass funnel. The liquid was collected with vigorous stirring over sodium sulfite (5%) (20 ml) in order to quench the reaction. The product was isolated by extraction with $CH_2Cl_2$, and washed with a saturated solution of $NaHCO_3$. The yellow oil which was obtained was dried over $MgSO_4$. Purification by flash chromatography (70/30, hexanes/EtOAc) afforded the phosphoramidate 10 as a yellow oil (0.130 g, 0.29 mmol, 44%).

'H-NMR ($CDCl_3$, 360 MHz) δ 7.12 (d,J=1.9 Hz, IH, ArH), 6.88 (dd, J=8.4 Hz, 2.0 Hz, IH, ArH), 6.72 (dd, J=8.4 Hz, 1.7, IH, ArH), 6.49 (s, 2H, ArH), 6.51 (d, J=12.1 Hz, IH, vinyl CH), 6.41 (d, J=12.1 Hz, IH,vinyl CH), 5.67 (d, J=10.0 Hz, NH), 4.02 (m, 4H, $CH_2$), 3.83 (s, 3 H, $OCH_3$), 3.83 (s, 3 H, $OC_3$), 3.68 (s, 6 H, $OCH_3$), 1.25 (t, 6 H, J=7.1 Hz, $CH_3$).

$^{13}$C-NMR ($CDCl_3$, 90 MHz) δ 152.7, 146.7, 146.6, 137.0, 132.7, 130.3, 129.7, 129.1, 129.0, 122.0, 117.0, 109.9, 106.0, 62.8, 60.7, 55.7, 16.1.

$^{31}$P-NMR ($CDCl_3$, 145 MHz) δ 0.84.

HRMS (EI) M+ calcd for $C_{22}H_{30}NO_7P$ 451.1760, found 451.1765.

EXAMPLE 1
Synthesis of the Indole-based Anti-tubulin Agents

Preparation of 2-Phenyl Indole 31

Method 1 (2 Steps)

To a well-stirred solution of KOH (0.926 g, 16.5 mmol) in EtOH (18 ml) and $H_2O$ (9 ml) at rt was added m-anisidine (2.192 g, 17.80 mmol) by syringe. The solution was then stirred at 0° C. After 10 min, the solution of 2-bromo-4-methoxyacetophenone (4.09 g, 17.80 mmol) was added dropwise with an addition funnel over a 40 minute period. After 24 h, 0° C. to rt, water was added. The product was isolated by extraction (I H HCI, NaHCO3, brine, MgSO4). The product was purified by recrystallization (50:50 EtOAc:hexanes) to afford secondary amine 30 (2.46 g, 9.07 mmol, 52%) as yellow solid.

'H NMR ($CDCl_3$): δ 7.98 (2H, D, J=8.9 Hz), 7.12 (IH, t, J 8.1 Hz), 6.97 (2H, d, J 8.9 Hz), 6.30 (3H, m), 4.54 (2H, s), 3.88 (3H, s), 3.79 (3H, s).

Polyphosphoric acid (PPA) was charged to a round-bottom flask and the temperature was raised to 80° C. with vigirous stirring. To this flask was added the foregoing amine 30 (4.0 g, 14.74 mmol) in 6 portions over a 30 minute period. After 2 h, 80° C. to 90° C., water was added. The product was isolated by extraction (EtOAc, $NaHCO_3$, brine, $MgSO_4$). Purification by recrystallization (acetone) afforded indole 31 (0.544 g, 2.15 mmol, 15%) as a pale yellow solid.

'H NMR ($CDCl_3$): δ 11.24 (IH, br, s), 7.72 (2H, d, J 8.82 Hz), 7.36 (IH, d, J=8.57 Hz), 7.00 (2H, d, J=8.84 Hz), 6.85 (IH, d, J=2.07 Hz), 6.66 (IH, d, J=1.66 Hz), 6.63 (IH, dd, J 8.59, 2.28 Hz), 3.78 (3H, s), 3.77 (3H, s).

$^{13}$C NMR ($CDCl_3$): δ 158.15, 155.22, 137.44, 136.33, 125.60, 124.93, 122.82, 120.04, 114.07, 109.00, 96.97, 94.01, 54.93, 54.88.

Method 2(1 Step)

To a boiling mixture of in-anisidine (1.56 ml, 20.0 minol) and N,N-dimethylaniline (3.5 ml) was added 2-bromo-4-methoxyacetophenone (1.37 g in EtOAc, 6.00 mmol) slowly by syringe. After addition, the mixture was kept at 170° C. for 1 hour. The reaction mixture was cooled to room temperature and a dark colored solid was formed. EtOAc was added along with HCI (2 N). The aqueous layer was extracted with EtOAc several times. The combined organic layers were washed with brine, and dried over $MgSO_4$. Solvent was removed under the reduced pressure to afford a dark brown colored solid. Purification by recrystallization in EtOH afforded indole 31 as a white crystallinc material.

'H NMR($CDCl_3$): δ 11.24 (IH,br,s),7.72(2H,d, J 8.82 Hz), 7.36 (IH,d, J 8.57 Hz),7.00 (2H,d, J=8.84 Hz), 6.85 (IH, d, J=2.07 Hz), 6.66 (IH, d, J=1.66 Hz), 6.63 (IH, dd, J8.59, 2.28 Hz),3.78 (3H, s), 3.77 (3H, s).

$^{13}$C NMR ($CDCl_3$): δ 158.15, 155.22, 137.44, 136.33, 125.60, 124.93, 122.82, 120.04, 114.07, 109.00, 96.97, 94.01, 54.93, 54.88.

Melting Point: 208–229.5° C.

HRMS (El) M+ calcd for $CH_{16}NO_2$ 253.3035, found 253.1060.

Preparation of Trimethoxybenzoate 2-Phenylindole 33

To a well stirred solution of indole 31 (0.502 g, 1.98 mmol) in o.dichlorobenzene (10 ml) was added trimethoxybenzoylchloride (0.692 g, 3.00 mmol). The reaction mixture was heated to reflux for 12 hours. Solvent was removed by distillation under reduced pressure. After cooling down to room temperature, a dark solid formed which was dissolved in chloroform and purified by silica gel column chromatography with chloroform as the eluent. The collected mixture was again purified by column chromatography (50:50 hexanes:EtOAc) affording trimethoxybenzyl indole 33 (0.744 g, 1.66 mmol, 84%) as a yellow oily gel. Pale yellow-green crystals were obtained by recrystallization from a mixture of ethanol and hexanes.

'H NMR ($CDCl_3$): δ 8.63 (IH, br, s), 7.88 (IH, d, J=9.39 Hz), 7.24 (2H, d, J=8.78 Hz), 6.95(2H, s), 6.90 (2H, m), 6.71 (2H, d, J=8.79 Hz), 3.86 (3H, s), 3.80 (3H, s), 3.73 (3H, s), 3.68 (6H, s);

$^{13}$C NMR ($CDCl_3$): δ 192.23, 159.73, 157.06, 152.42, 142.85, 141.01, 136.41, 134.65, 130.16, 124.28, 122.94, 122.17, 113.67, 112.46, 111.52, 107.24, 94.54, 60.78, 55.92, 55.54, 55.14.

Melting Point: 153–155° C.

Anal. Calcd for $C_{26}H_{25}NO_6$: C, 69.79; H, 5.63; H, 3.13. Found: C, 69.6 1; H, 5.63; N, 3.01.

EXAMPLE 2

Inhibition of Tubulin Polymerization Assay $IC_{50}$ values for tubulin polymerization were determined according to the procedure described in Bai et al. Purified tubulin is obtained from bovine brain cells as described in Hamel and Lin. Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mlM $MgCl_2$, 4% DMSO and 0.1M 4-morpholineethanesulfonate buffer (MES, pH 6.4). $IC_{50}$ is the amount of inhibitor needed to inhibit tubulin polymerization 50% with respect to the amount of inhibition that occurs in the absence of inhibitor. The $IC_{50}$ value determined for 3-(3',4',5'-trimethoxybenzoyl)-2-(4'-methoxyphenyl)-6-methoxyindole was 0.5–1.5 $\mu$M.

EXAMPLE 3

Cytotoxic Assay with P388 Leukemia Cells

One of the newly prepared compounds was evaluated for cytotoxic activity against P388 leukemia cells using an assay system similar to the National Cancer Institute procedure described below and in Monks et al. The ED50 value (defined as the effective dosage required to inhibit 50% of cell growth) of 3-(3',4',5' trimethoxybenzoyl)-2-(4'-methoxyphenyl)-6-methoxyindole was found to be 0.0133 $\mu$g/mL.

EXAMPLE 4

Growth Inhibitory Activity Against Other Cancer Cell Lines 3-(3',4',5'-Trimethoxybenzoyl)-2-(4'-methoxyphenyl)-6-methoxyindole was evaluated in terms of growth inhibitory activity against several human cancer cell lines, including pancreas, ovarian, CNS, lung-NSC, colon, and prostate lines. The assay used is described in Monks et al. Briefly, the cell suspensions, diluted according to the particular cell type and the expected target cell density (5,000–40,000 cells per well based on cell growth characteristics), were added by pipet (100 $\mu$l) to 96-well microtiter plates. Inoculates were allowed a preincubation time of 24–28 hours at 37° C. for stabilization. Incubation with the inhibitor compounds lasted for 48 hours in 5% $CO_2$ atmosphere and 100% humidity. Determination of cell growth was done by in situ fixation of cells, followed by staining with a protein-binding dye, sulforhodamine B (SRB), which binds to the basic amino acids of cellular macromolecules. The solubilized stain was measured spectrophotometrically. The results of these assays are shown in Table 1. $GI_{50}$ is defined as the dosage required to inhibit tumor cell growth by 50%.

TABLE IV

Activity of Indole Ligand Against Selected Human Cancer Cell lines (In Vitro).

| CELL TYPE | CELL LINE | Indole-based Ligand 33 $GI_{50}$ ($\mu$G/mL) |
| --- | --- | --- |
| Pancreas-a | BXPC-3 | $2.0 \times 10^{-3}$ |
| Ovarian | OVCAR-3 | $2.4 \times 10^{-3}$ |
| CNS | SF-295 | $2.4 \times 10^{-3}$ |
| Lung-NSC | NCI-H460 | $2.6 \times 10^{-3}$ |
| Colon | KM20L2 | $1.7 \times 10^{-3}$ |
| Prostate | DU-145 | $2.3 \times 10^{-3}$ |

TABLE IV-continued

Indole and indole containing compounds of therapeutic efficacy have been known for many, many years. What is truly unique about the indole compounds described in this application is the fact that these compounds are the first (to the best of our knowledge) indole-based ligands to incorporate the 3,4,5-trimethoxyaryl motif reminiscent of colchicine and combretastatin A-4 arranged in an appropriate molecular conformation such that a pseudo aryl-aryl pi stacking interaction can take place. It is our contention that such an aryl-aryl interaction of the appropriate centroid-to-centroid distance (approximately 4.7 Å) is imperative for enhanced binding affinity to the colchicine site on β-tubulin. It is this binding that ultimately leads to an inhibition of tubulin polymerization which manifests itself as a cytotoxic event. It should be readily apparent to any practitioner skilled in the art that there are various ways of appending trimethoxyaryl and trimethoxyaroyl groups around an indole molecular scaffold in a manner which will result in a similar molecular conformation capable of undergoing pseudo pi-pi stacking. In addition, although the trimethoxyaryl motif seems optimal for enhanced tubulin binding, it is also very possible that another combination of alkoxy substituents (such as ethoxy, propoxy, isopropoxy, allyloxy, etc.) either as a trisubstituted pattern or as disubstituted (with one type of alkoxy moiety) and monosubstituted (with a different alkoxy moiety), or with three distinct types of alkoxy moieties may also have good tubulin binding characteristics. It is also conceivable that instead of having aryl alkoxy groups, it may be possible to substitute simply aryl-alkyl and aryl-alkenyl moieties and still maintain the enhanced cytotoxicity profile. Phenolic groups may also have activity on these described indole ligands. The synthesis of any of these modified indole-ligands will be very straight-forward for anyone skilled in the art, and often will only involve a different choice of initial starting materials. To prepare these alternative ligands, the same synthetic schemes (FIGS. 6, 9, 11, 12–16), or similar schemes with only slight modifications may be employed. In previous studies with the benzo[b]thiophene ligands, we have demonstrated that the carbonyl group can be replaced with an oxygen to generate a new compound which maintains the same or similar biological efficacy with tubulin. Similarly, the replacement of the carbonyl group in the described indole ligand may be replaced with an oxygen atom (ether linkage) to generate anew derivative which would be predicted to have good activity with tubulin. This compound may be prepared by an addition elimination reaction utilizing the trimethoxyphenolic anion as a nucleophile as described by us for the benzo[b]thiophene compounds. Other linkage atoms between the aryl aryl rings are conceivable as well.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Literature Cited 1) (a) For a recent review of numerous antitubulin and antimitotic agents see: Hamel, E., Antimitotic Natural Products and Their Interactions with Tubulin, *Medicinal Research Reviews*, 1996, 16, 207.

(b) Gerwick, W. H.; Proteau, P. J.; Nagle, D. G.; Hamel, B.; Blokhin, A.; Slate, D. L., Structure of Curacin A, a Novel Antimitotic, Antiproliferative, and Brine Shrimp Toxic Natural Product from the Marine *Cyanobacterium Lyngbya majuscula, J. Org. Chem.* 1994, 59, 1243.

(c) Gianna Kakou, P.; Sackett, D.; Fojo, T.; Tubulin/Microtubes: Still a promising Target for New Chemotherapeutic Agents, *J. Natl Cancer Inst.*, 2000, 92, 182.

2) Owellen, R. J.; Hartkc, C. A.; Kickerson, R. M.; Hams, F. O., Inhibition of Tubulin-Microtubule Polymerization by Drugs of the Vinca Alkaloid Class, *Cancer Res.* 1976, 36, 1499.

3) Lavielle, G.; Havtefaye, P.; Schaeffer, C.; Boutin, J. A.; Cudennec, C. A.; Pierre, A., New α-Amino Phosphonic Acid Derivatives of Vinblastine: Chemistry and Antitumor Activity, *J Med Chem.* 1991, 34, 1998.

4) (a) Kingston, D. G. I.; Samaranayake, G.; Ivey, C. A., The Chemistry of Taxol, a Clinically Useful Anticancer Agent, *J. Nat. Prod.* 1990, 53, 1.

(b) Schiff, P. B.; Fant, J.; Horwitz, S. B., Promotion of Microtubule Assembly In Vitro by Taxol, *Nature*, 1979, 277, 665.

(c) Swindell, C. S.; Krauss, N. B.; Horwitz, S. B.; Ringel, I., Biologically Active Taxol Analogs with Deleted A-ring Side Chain Substituents and Variable C-2Æ Configurations, *J. Med Chem.* 1991, 34, 1176.

(d) Pamess, J.; Horwitz, S. B., Taxol Binds to Polymerized Tubulin In Vitro, *J. Cell Biol.* 1981, 91, 479.

5) (a) Nakada, M.; Kobayashi, S.; Iwasaki, S.; Ohno, M., The First Total Synthesis of the Antitumor Macrolide Rhizoxin: Synthesis of the Key Building Blocks, *Tetrahedron Lett.* 1993,34,1035.

(b) Nakada, M.; Kobayashi, S.; Iwasaki, S.; Ohno, M., The First Total Synthesis of the Antitumor Macrolide Rhizoxin, *Tetrahedron Lett.* 1993, 34, 1039.

(c) Boger, D. L.; Curran, T. T., Synthesis of the Lower Subunit of Rhizoxin, *J. Org. Chem.* 1992, 57, 2235.

(d) Rao, A. V. R; Sharma, G. V. M.; Bhanu, M. N., Radical Mediated Enantioselective Construction of C-1 to C-9 Segment of Rhizoxin, *Tetrahedron Lett.* 1992, 33, 3907.

(e) Kobayashi, S.; Nakada, M.; Ohno, M., Synthetic Study on an Antitumor Antibiotic Rhizoxin by Using an Enzymatic Process on Prochiral betaSubstituted Glutarates, *Pure Appl. Chem.* 1992, 64, 1121.

(f) Kobayashi, S.; Nakada, M.; Ohno, M., Synthetic Study on an Antitumor Antibiotic Rhizoxin by Using an Enzymatic Process on Prochiral betasubstituted Glutarates Indian J. Chem., Sect. B. 1993, 32B, 159.

(g) Rao, A. V. R.; Bhanu, M. N.; Sharma, G. V. M., Studies Directed Towards the Total Synthesis of Rhizoxin: Stereoselective Synthesis of C-12 to C-18 Segment, *Tetrahedron Lett.* 1993, 34, 707.

6) (a) Lin, C. M.; Ho, H. H.; Pettit, G. R.; Hamel, E., Antimitotic Natural Products Combretastatin A-4 and Combretastatin A-2: Studies on the Mechanism of Their Inhibition of the Binding of Colchicine to Tubulin, *Biochemistry* 1989, 28, 6984.

(b) Pettit, G. R; Cragg, G. M.; Singh, S. B., Antineoplastic agents, 122. Constituents of Combretum caffrum, *J. Nat. Prod* 1987, 50, 386.

(c) Pettit, G. R.; Singh, S. B.; Cragg, G. M., Synthesis of Natural (−)Combretastatin, *J. Org. Chem.* 1985, 50, 3404.

(d) Pettit, G. R.; Cragg, G. M.; Herald, D. L.; Schmidt, J. M.; Lohavanijaya, P., Isolation and Structure of combretastatin, *Can. J. Chem.* 1982, 60, 1374.

(e) Dorr, R. T.; Dvorakova, K.; Snead, K., Alberts, D. S.; Salmon, S. E.; Pettit, G. R, Antitumor Activity of Combretastatin A4 Phosphate, a Natural Product Tubulin Inhibitor, *Invest. New Drugs*, 1996, 14, 131.

7) (a) Hammonds, T. R.; Denyer, S. P.; Jackson, D. B.; Irving, W. L., Studies To Show That With Podophyllotoxin the Early Replicative Stages of Herpes Simplex Virus Type I Depend Upon Functional Cytoplasmic Microtubules, *J. Med. Microbiol.*, 1996, 45, 167.

(b) Cortese, F.; Bhattacharyya, B.; Wolff, J., Podophyllotoxin as a Probe for the Colchicine Binding Site of Tubulin, *J. Biol. Chem.*, 1977, 252, 1134.

8) Nicolaou, K. C., Winssinger, N., Pastor, J., Ninkovic, S., Sarabia, F., He, Y., Vourloumis, D., Yang, Z., Oi, T., Giannakakou, P., Hamel, B., Sythesis of Epothilones A and B in Solid and Solution Phase, *Nature*, 1997, 387, 268–272.

9) (a) Pettit, G. R., Kamano, Y., Herald, C. L., Tuinman, A. A., Boettner, F. E., Kizu, H., Schmidt, J. M., Baczynskyj, L., Tomer, K. B., Bontems, R. J., The Isolation and Structure of a Remarkable Marine Animal Antineoplastic Contituent: Dolastatin 10, *J. Am. Chem. Soc.*, 1987, 109, 6883–6885.

(b) Pettit, G. R., Srirangam, J. K., Barkoczy, J., Williams, M. D., Boyd, M. R., Hamel, E., Pettit, R. K., Hogan F., Bai, R., Chapuis, J. C., McAllister, S. C., Schmidt, J. M., Antineoplastic Agents 365: Dolastatin 10 SAR Probes, *Anti-Cancer Drug Des.*, 1998, 13, 243–277.

10) Zhang, X.; Smith, C. D., Microtubule Effects of Welwistatin, a Cyanobacterial Indolinone that Circumvents Multiple Drug Resistance, *Molecular Pharmacology*, 1996, 49, 288.

11) Pettit, G. R., Told, B., Herald, D. L., Verdier-Pinard, P., Boyd, M. R., Hamel, E., Pettit, R. K., Antineoplastic Agents 379. Synthesis of phenstatin Phosphate, *J. Med Chem.*, 1998, 41, 1688–1695.

12) Jiang, J. B.; Hesson, D. P.; Dusak, B. A.; Dexter, D. L.; Kang, G. J.; Hamel, B., Synthesis and Biological Evaluation of 2-Styrylquinazolin-4(3H)-ones, a New Class of Antimitotic Anticancer Agents Which Inhibit Tubulin Polymerization, *J. Med. Chem.* 1990, 33, 1721.

13) Cushman, M.; Nagarathnam, D.; Gopal, D.; Chakraborti, A. K.; Lin, C. M.; Hamel, E. Synthesis and Evaluation of Stilbene and Dihydrostilbene Derivatives as Potential Anticancer Agents That Inhibit Tubulin Polymerization, *J. Med Chem.* 1991, 34, 2579.

14) (a) Sawada, T.; Kato, Y.; Kobayashi, H.; Hashimoto, Y.; Watanabe, T.; Sugiyama, Y.; Iwasaki, S., A Fluorescent Probe and a Photoaffinity Labeling Reagent to Study the Binding Site of Maytansine and Rhizoxin on Tubulin, *Bioconjugate Chem.*, 1993, 4, 284.

(b) Rao, S.; Horwitz, S. B.; Ringel, I., Direct Photoaffinity Labeling of Tubulin with Taxol, *J. Natl. Cancer Inst.*, 1992, 84, 785.

(c) Chavan, A. J.; Richardson, S. K.; Kim, H.; Haley, B. E.; Watt, D. S., Forskolin Photoaffinity Probes for the Evaluation of Tubulin Binding Sites, *Bioconjugate Chem.* 1993, 4, 268.

(d) Sawada, T.; Kobayashi, H.; Hashimoto, Y.; Iwasaki, S., Identification of the Fragment Photoaffinity-labeled with Azidodansyl-rhizoxin as Met-363-Lys-379 on beta-Tubulin, *Biochem. Pharmacol.* 1993, 45, 1387.

(e) Staretz, M. E.; Hastie, S. B., Synthesis, Photochemical Reactions, and Tubulin Binding of Novel Photoaffinity Labeling Derivatives of Coichicine, *J. Org. Chem.* 1993, 58, 1589.

(f) Hahn, K. M.; Hastie, S. B.; Sundberg, R. J., Synthesis and Evaluation of 2-Diazo-3,3,3-trifluoropropanoyl Derivatives of Colchicine and Podophyllotoxin as Photoaffinity Labels: Reactivity, Photochemistry, and Tubulin Binding, *Photochem. Photobiol.* 1992, 55, 17.

(g) Sawada, T.; Hashimoto, Y.; Li, Y.; Kobayashi, H.; Iwasaki, S., Fluorescent and Photoaffinity Labeling Derivatives of Rhizoxin, *Biochem. Biophys. Res. Commun.* 1991, 178, 558.

(h) Wolff, J.; j(nipling. L.; Cahnmann, H. J.; Palumbo, G., Direct Photoaffinity Labeling of Tubulin with Coichicine, *Proc. Natl. Acad Sci. USA.* 1991, 88, 2820.

(i) Floyd. L. J.; Bames, L. D.; Williams, R. F., Photoaffinity Labeling of Tubulin with (2-Nitro-4-azidophenyl) deacetylcolchicine: Direct Evidence for Two Colchicine Binding Sites, *Biochemistry,* 1989, 28, 8515.

(j) Safa, A. R.; Hamel, E.; Felsted, R. L., Photoaffinity Labeling of Tubulin Subunits with a Photoactive Analog of Vinblastine, *Biochemisty* 1987, 26, 97.

(k) Williams, R. F.; Mumford, C. L.; Williams, G. A.; Floyd, L. J.; Aivaliotis, M. J.; Martinez, R A.; Robinson, A. K.; Bames, L. D., A Photoaffinity Derivative of Colchicine: 6-(4'-Azido-2'-nitrophenylamino) hexanoyldeacetylcolchicine. Photolabeling and Location of the Colchicine-binding Site on the alpha-subunit of Tubulin, *J. Biol. Chem.* 1985, 260, 13794.

15) Nogales, E., Wolf, S. G., and Downing, K. H., Structure fo the ct,~Tubulin Dimer by Electron Crystallography, *Nature,* 1998, 391, 199–203.

16) Shirai, R.; Tokuda, K.; Koiso, Y.; Iwasaki, S., Synthesis and AntiTubulin Activity of Aza-Combretastatins, *Biomedical Chem. Lett.* 1994, 699.

17) (a) Jones, C. K.; Jevnikar, M. G.; Pike, A. J.; Peters, M. K; Black, L. J.; Thompson, A. R.; Falcone, J. F.; Clemens, J. A., Antiestrogens. 2. Structure-Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]phenylimethanone Hydrochloride (LY156758), a Remarkably Effective Estrogen Antagonist with Only Minimal Intrinsic Estrogenicity, *J. Med Chem.* 1984, 27, 1057.

(b) Grese, T. A.; Cho, S.; Finley, D. R.; Godfrey, A. G.; Jones, C. D.; Lugar III, C. W.; Martin, M. J.; Matsumoto, K.; Pennington, L. D.; Winter, M. A.; Adrian, M. D.; Cole, H. W.; Magee, D. E.; Phillips, D. L.; Rowley, E. R.; Short, L.; Glasebrook, A. L.; Bryant, H. R., Structure-Activity Relationships of Selective Estrogen Receptor Modulators: Modifications to the 2-Arylbenzothiophene Core of Raloxifene, *J Med Chem.*, 1997, 40, 146.

(c) Palkowitz, A. D.; Glasebrook, A. L.; Thrasher, K. J.; Hauser, K. L.; Short, L. L.; Phillips, D. L.; Muehl, B. S.; Sato, M.; Shetler, P. K.; Cullinan, G. J.; Pell, T. R.; Bryant, H. U., Discovery and Synthesis of [6-Hydroxy-3-[4-[2-(1-piperidinyl)ethoxy]phenoxy]-2-(4-hydroxyphenyl)]benzo[b]thiophene: A Novel, Highly Potent, Selective Estrogen Receptor Modulator, *J. Med Chem.,* 1997, 40, 1407.

18) Pinney, K. G., Anti-Mitotic Agents Which Inhibit Tubulin Polymerization, Baylor University, Application for United States Letters Patent, Filed, Mar. 6, 1997. U.S. Pat. No. 5,886,025. Issued, Mar. 23, 1999.

19) Pinney, K. G.; Mejia, P.; Mocharla, V. P.; Shirlai, A.; Pettit, G. R., Anti-Mitotic Agents Which Inhibit Tubulin Polymerization, PCT Application Pending, filed under the Patent Cooperation Treaty on Mar. 6, 1998 and designating all PCT member states. Filed jointly by Baylor University, Arizona Disease Control Research Commission, and Arizona State University.

20) Mullica, D. F.; Pinney, K. G.; Mocharla, V. P.; Dingeman, K. M.; Bounds, A. D.; Sappenfield, E. L., Characterization and Structural Analyses of Trimethoxy and Triethoxybenzo[b]thiophene, *J. Chem. Cryst.,* 1998, 28, 289–295.

21) Pmnney, K. G.; Dingeman, K. D.; Bounds, A. D.; Mocharla, V. P.; Pettit, G. R.; Bai, R.; Hamel, E., A New Anti-Tubulin Agent Containing the Benzo[b]thiophene Ring System, *Bioorganic and Medicinal Chemistry Letters,* 1999, 9, 1081–1086.

22) (a) D'Amato, R. J.; Lin, C. M.; Flynn, E.; Folkman, J.; Hamel, E., 2Methoxyestradiol, an endogenous mamalian metabolite, inhibits tubulin polymerization by interacting at the colchicine site, *Proc. Natl. Acad Sci.* 1994, 91, 3964.

(b) Cushman, M.; He, H-M.; Katzenellenbogen, J. A.; Lin, C. M.; Hamel, E., Synthesis, Antitubulin and Antimitotic Activity, and Cytotoxicity of Analogs of 2-Methoxyestradiol, an Endogenous Mammalian Metabolite of Estradiol That inhibits Tubulin Polymerization by Binding to the Colchicine Binding Site, *J. Med Chem.,* 1995, 38, 2041.

(c) Hamel, E.; Lin, C. M.; Flynn, E.; DÆ Amato, R. J. D., Interactions of 2-Methoxyestradiol, and Endogenous Mammalian Metabolite, with Unpolymerized Tubulin and with Tubulin Polymers, *Biochemistry,* 1996, 35, 1304.

(d) Cushman, M.; He, H.-M.; Katzenellenbogen, J. A.; Varma, R. K.; Hamel, E.; Lin, C. M.; Ram, S.; Sachdeva, Y. P., Synthesis of Analogs of 2-Methoxyestradiol with Enhanced Inhibitory Effects on Tubulin Polymerization and Cancer Cell Growth, *J. Med Chem.,* 1997, (in press).

23) Boyd, M. R.; Paull, K. D., Some Practical Considerations and Applications of the National Cancer Institute In Vitro Anticancer Drug Discovery Screen, *Drug Development Research,* 1995, 34, 91.

24) Dark, G. G., Hill, S. A., Prise, V. G., Tozer, G. M., Pettit, G. R., Chaplin, D. J., Combretastatin A-4, an Agent That Displays Potent and Selective Toxicity Toward Tumor Vasculature, *Cancer Res.,* 1997, 57, 1829–1834.

25) Angerer, E.; Prekajac, J.; Strohmeier, J.; *J. Med Chem.* 1984, 27, 1439–1447.

26) Inion, H.; Vogelaer, H.; Bauthier, J.; Colot, M.; Richard, J.; *Eur. J. Med. Chem.* 1977, 5, 483–487.

27) Gastpar, R.; Goldbrunner, M.; Marko, D.; von Angerer, E., MethoxySubstituted 3-Formyl-2-phenylindoles Inhibit Tubulin Polymerization, *J. Med. Chem.* 1998, 41, 4965–4972.

28) Taylor, S. D.; Chen, M, J,; Dinaut, A. N.; and Batey, R. A., *Tetrahedron* 1998, 54, 4223–4242.

29) Fischer, B.; and Sheihet, L., *J. Org. Chem.* 1998, 63, 393–395.

30) Cell line studies carried out through collaborative efforts with Prof. George R. Pettit; Arizona State University; Tempe; Ariz.

31) Pettit, G. R.; Toki, B.; Herald, D. L.; Verdier-Pinard, P.; Boyd, M. R.; Hamel, E.; and Pettit, R. K., *J. Med Chem.* 1998, 41, 1688–1695.

32) Tubulin polymerization studies carried out through collaborative efforts with Dr Ernest Hamel, National Institute of Health, National Cancer Institute.

33) Pettit, G. R.; and Rhodes, M. R.,*Anti-Cancer Drug Des.* 1998, 13, 183–191.

34) Dark, G. G.; Hill, S. A.; Prise, V. E.; Tozer, G. M.; Pettit, G. R.; and Chaplin, D. J., *Cancer Res.* 1997, 57; 1829–1834.

35) Iyer, S.; Chaplin, D. J.; Rosenthal, D. S.; Boulares, A. H.; Li, L. Y.; and Smulson, M. E., *Cancer Res.* 1998, 58, 4510–4514.

36) Pinney et al., Tubulin Binding Ligands and Corresponding Prodrug Constructs, Provisional Patent Application, U.S. Ser. No. 60/188,295, filed on Mar. 10, 2000.

37) Pinney et al., Synthesis of a Benzo[b]thiophene-based Vascular Targeting Prodrug and Related Anti-Tubulin Ligands, 220*th American Chemical Society, National Meeting*, Division of Organic Chemistry, Abstract No. 196, Washington, D.C., Aug. 20–24, 2000.

What is claimed is:

1. A compound of the structure:

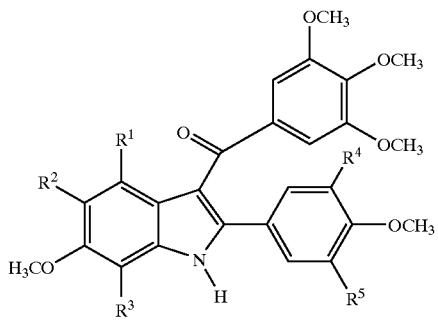

wherein
R$^1$ through R$^5$ contain at least one hydroxyl group or at least one amine group (NH$_2$, NHR$^6$, or NR$^6$R$^7$ where R$^6$ and R$^7$ are the same or different alkyl having up to 8 carbon atoms), while the remaining R$^1$ through R$^5$ are hydrogen.

2. A compound of the structure:

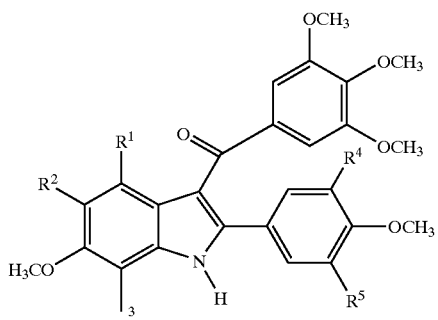

wherein
R$^1$ through R$^5$ contain at least one phosphate ester (—OP(O)(O$^-$M$^+$)$_2$) or a phosphoramidate (—NP(O)(O$^-$M$^+$)$_2$) where M is a cation or (—NP(O)(OR)$_2$) where R is an alkyl with up to 8 carbon atoms (the two R groups are the same or different), while the remaining R$^1$ through R$^5$ are hydrogen.

3. A compound of the structure:

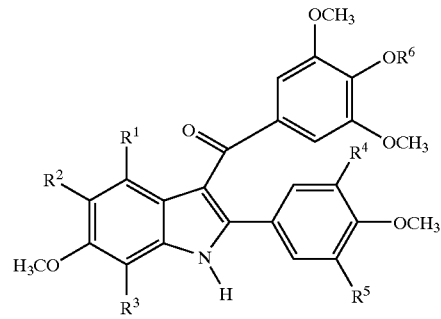

wherein
R$^1$ through R$^5$ contain at least one phosphate ester (—OP(O)(O$^-$M$^+$)$_2$) or a phosphoramidate (—NP(O)(O$^-$M$^+$)$_2$) where M is a cation or (—NP(O)(OR)$_2$) where R is an alkyl with up to 8 carbon atoms (the two R groups are the same or different), while the remaining R$^1$ through R$^5$ are hydrogen, and R$^6$ is hydrogen or alkyl.

4. A compound of the structure:

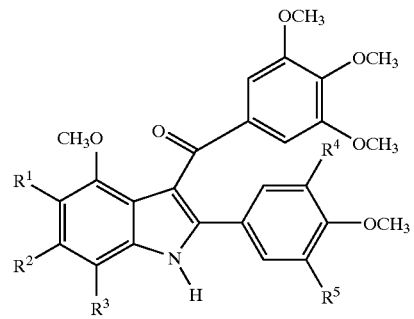

wherein
R$^1$ through R$^5$ contain at least one hydroxyl or at least one amine (NH$_2$, NHR$^6$, or NR$^6$R$^7$ where R$^6$ and R$^7$ the same or different alkyl having up to 8 carbon atoms) while the remaining R$^1$ through R$^5$ are a hydrogen.

5. A compound of the structure:

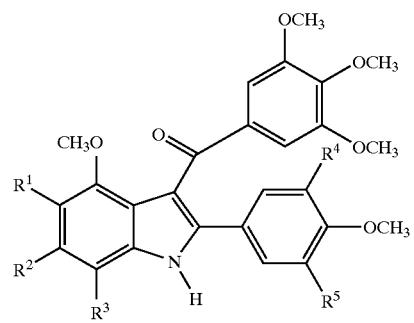

wherein
R$^1$ through R$^5$ contain at least one phosphate ester (—OP(O)(O$^-$M$^+$)$_2$) or a phosphoramidate (—NP(O)(O$^-$M$^+$)$_2$) where M is a cation or (—NP(O)(OR)$_2$) where R is an alkyl with up to 8 carbon atoms (the two R groups are the same or different), while the remaining R$^1$ through R$^5$ are hydrogen.

6. A compound of the structure:

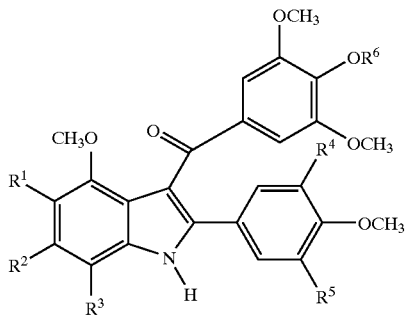

wherein
R¹ through R⁵ contain at least one phosphate ester (—OP(O)(O⁻M⁺)₂) or a phosphoramidate (—NP(O)(O⁻M⁺)₂) where M is=a cation or (—NP(O)(OR)₂) where R is an alkyl with up to 8 carbon atoms (the two R groups are the same or different), while the remaining R¹ through R⁵ are a hydrogen and R⁶ is hydrogen or alkyl.

7. A compound of the structure:

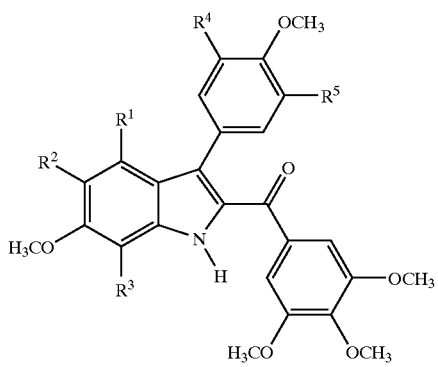

wherein
R¹ through R⁵ contain at least one hydroxyl group or at least one amine group (NH₂, NHR⁶ or NR⁶R⁷ where R⁶ and R⁷ are the same or different alkyl having up to 8 carbon atoms) while the remaining R¹ through R⁵ are a hydrogen.

8. A compound of the structure:

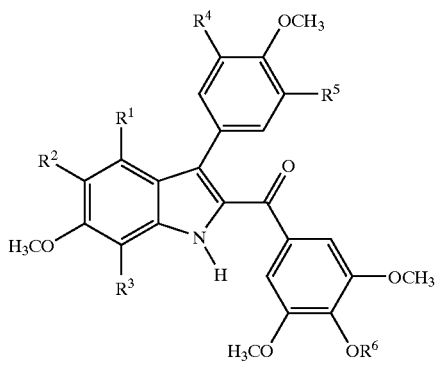

wherein
R¹ through R⁵ contain at least one phosphate ester (—OP(O)(O⁻M⁺)₂) or a phosphoramidate (—NP(O)(O⁻M⁺)₂) where M is a cation or (—NP(O)(OR)₂) where R is an alkyl with up to 8 carbon atoms (the two R groups are the same or different), while the remaining R¹ through R⁵ are hydrogen.

9. A compound of the structure:

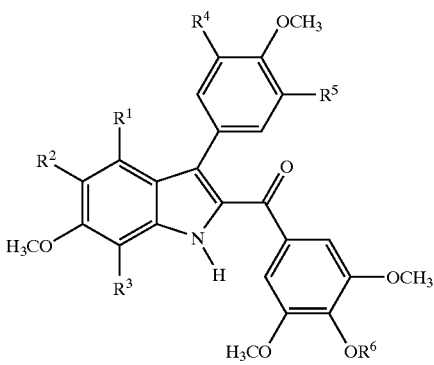

wherein
R¹ through R⁵ contain at least one phosphate ester (—OP(O)(O⁻M⁺)₂) or phosphoramidate (—NP(O)(O⁻M⁺)₂) where M is a cation or (—NP(O)(OR)₂) where R is an alkyl with up to 8 carbon atoms (the two R groups are the same or different), while the remaining R¹ through R⁵ are hydrogen, and R⁶ is hydrogen or alkyl.

10. A compound of the structure:

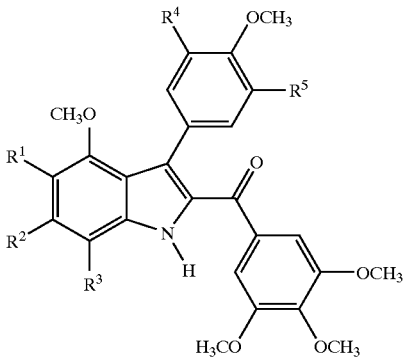

wherein
R¹ through R⁵ contain at least one hydroxyl group or at least one amine group (NH₂, NHR⁶, or NR⁶R⁷ where R⁶ and R⁷ are the same or different alkyl having up to 8 carbon atoms, benzyl, or aryl) while the remaining R¹ through R⁵ are a hydrogen.

11. A compound of the structure:

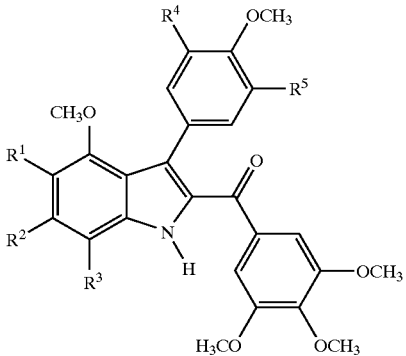

wherein
R¹ through R⁵ contain at least one phosphate ester (—OP(O)(O⁻M⁺)₂) or a phosphoramidate (—NP(O)(O⁻M⁺)₂) where M is a cation or (—NP(O)(OR)²) where R is an alkyl with up to 8 carbon atoms (the two R groups are the same or different), while the remaining R¹ through R⁵ are hydrogen.

12. A compound of the structure:

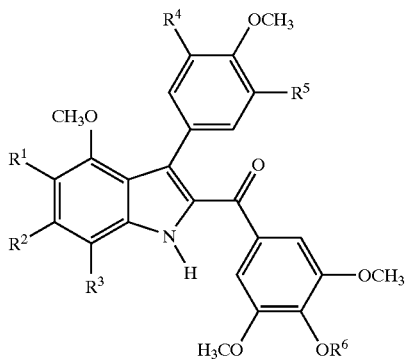

wherein
$R^1$ through $R^5$ contain at least one phosphate ester (—OP(O)(O⁻M⁺)₂) or a phosphoramidate (—NP(O)(O⁻M⁺)₂) where M is a cation or (—NP(O)(OR)²) where R is an alkyl with up to 8 carbon atoms (the two R groups are the same or different), while the remaining $R^1$ through $R^5$ are hydrogen, and $R^6$ is hydrogen or alkyl.

13. A compound of the structure:

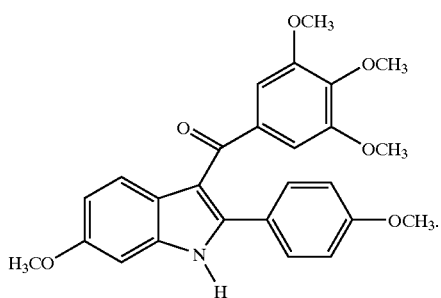

14. A compound of the structure:

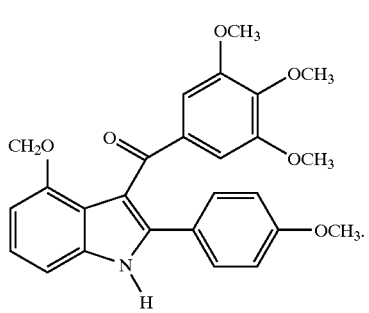

15. A compound of the structure:

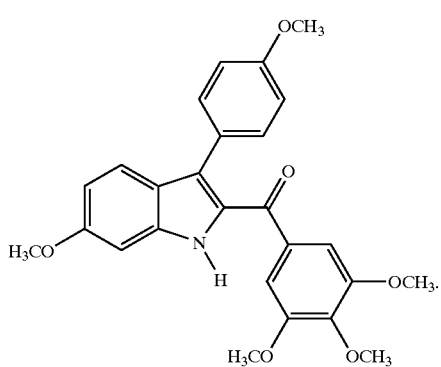

16. A compound of the structure:

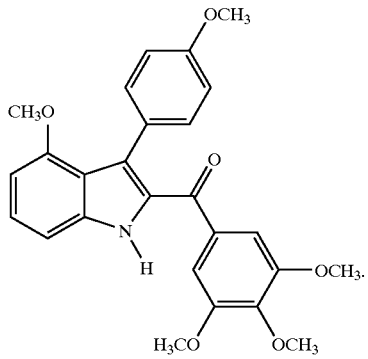

17. A compound of the structure:

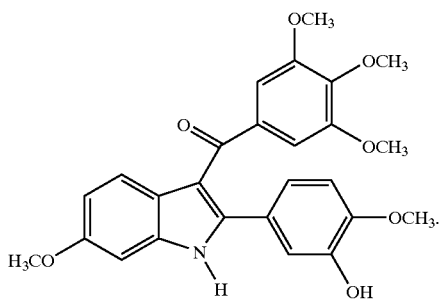

18. A compound of the structure:

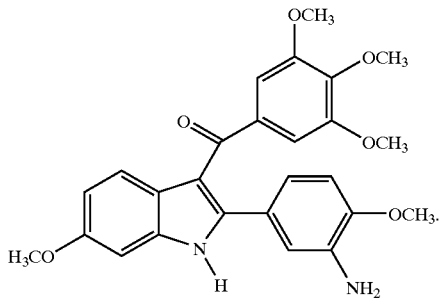

19. A compound of the structure:

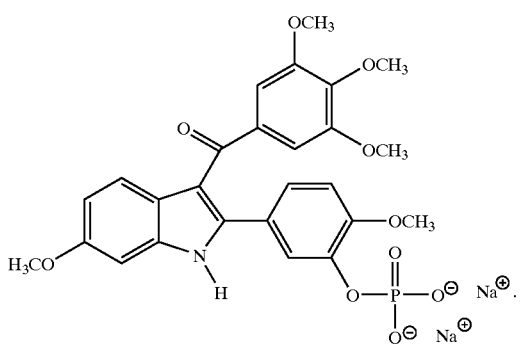

20. A compound of the structure:
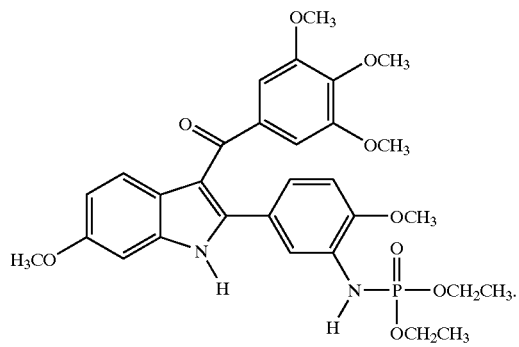
21. A compound of the structure:
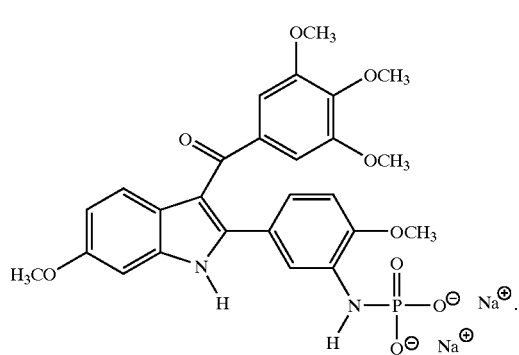
22. A compound of the structure:
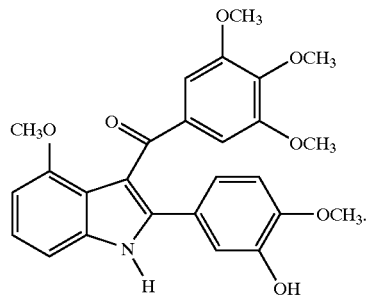
23. A compound of the structure:
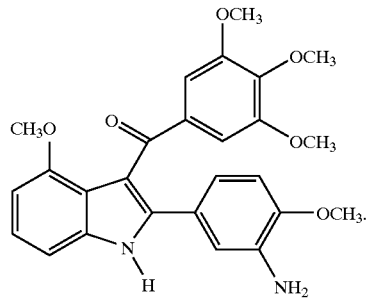
24. A compound of the structure:
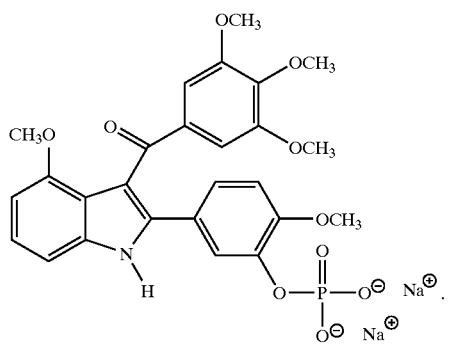
25. A compound of the structure:
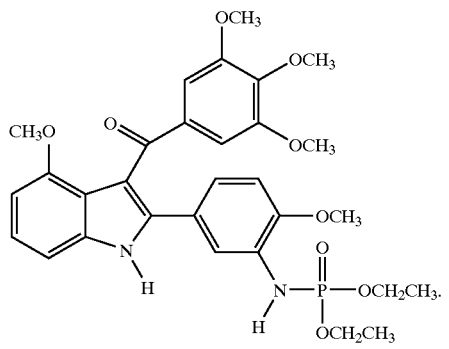
26. A compound of the structure:
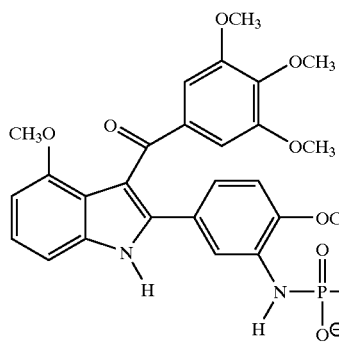
27. A compound of the structure:
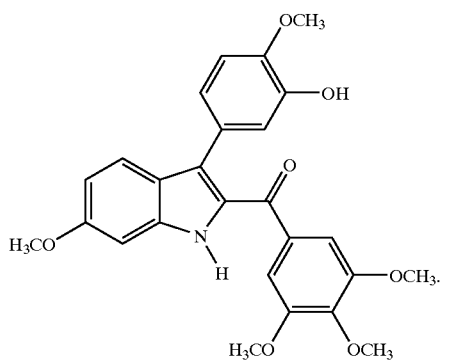

28. A compound of the structure:
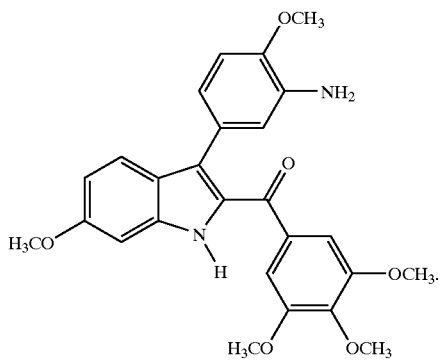
29. A compound of the structure:
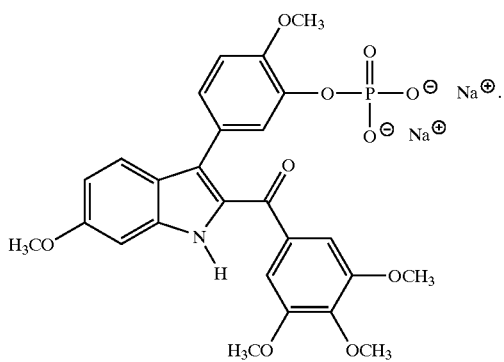
30. A compound of the structure:
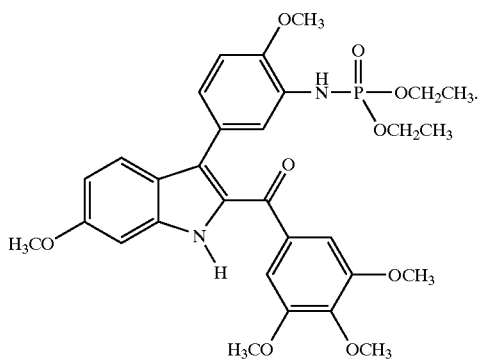
31. A compound of the structure:
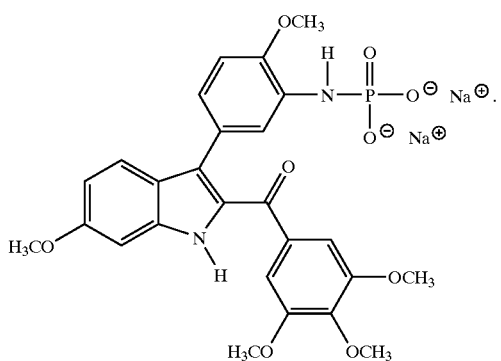
32. A compound of the structure:
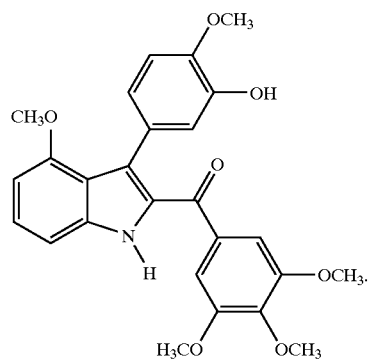
33. A compound of the structure:
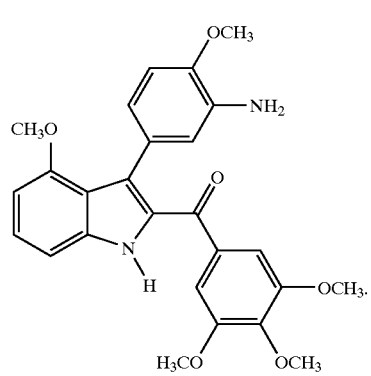
34. A compound of the structure:
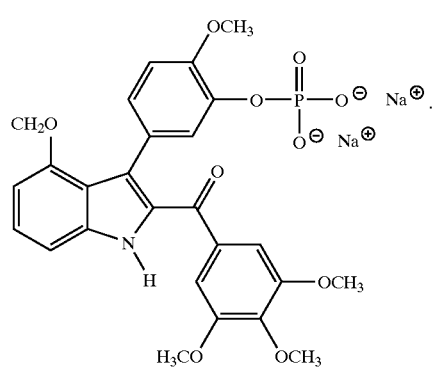
35. A compound of the structure:
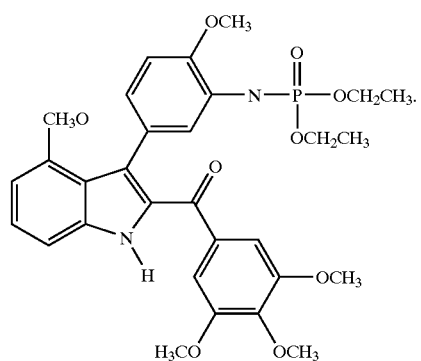

36. A compound of the structure:

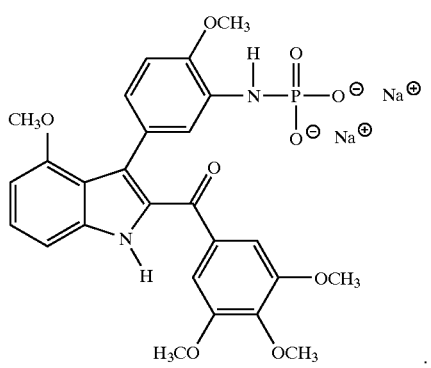

37. A method for inhibiting tubulin polymerization in vitro by contacting a tumor cell with an effective amount of a compound described in any one of claims 1–36.

38. A method for treating cancer by administering to a patient in need thereof, a therapeutically effective amount of a compound described in any one of claims 1–36, wherein said cancer is selected from the group consisting of leukemia, lung cancer, colon cancer, CNS cancer, ovarian cancer, prostate cancer, and pancreatic cancer.

39. A pharmaceutical composition comprising a compound from any one of claims 1–36 as an active component along with a pharmaceutically acceptable carrier.

* * * * *

UNITED STATES PATENT AND TRADEMARK OFFICE
CERTIFICATE OF CORRECTION

PATENT NO. : 6,849,656 B1
DATED : February 1, 2005
INVENTOR(S) : Pinney et al.

It is certified that error appears in the above-identified patent and that said Letters Patent is hereby corrected as shown below:

Column 18,
Lines 41-45, should read,
-- wherein
$R^1$ through $R^5$ contain at least one hydroxyl or at least one amine ($NH_2$, $NHR^6$, or $NR^6R^7$ where $R^6$ and $R^7$ are the same or different alkyl having up to 8 carbon atoms) while the remaining $R^1$ and $R^5$ are a hydrogen. --.

Column 19,
Lines 15-22, should read,
-- wherein
$R^1$ through $R^5$ contain at least one phosphate ester ($-OP(O)(O^-M^+)_2$) or a phosphoramidate ($-NP(O)(O^-M^+)_2$) where M is a cation or ($-NP(O)(OR)_2$) where R is an alkyl with up to 8 carbon atoms (the two R groups are the same or different), while the remaining $R^1$ through $R^5$ are a hydrogen and $R^6$ is hydrogen or alkyl. --.

Signed and Sealed this

Fourth Day of October, 2005

JON W. DUDAS
*Director of the United States Patent and Trademark Office*